(12) United States Patent
De Smedt et al.

(10) Patent No.: US 8,852,198 B2
(45) Date of Patent: Oct. 7, 2014

(54) SURGICAL GUIDING TOOL, METHODS FOR MANUFACTURE AND USES THEREOF

(75) Inventors: Karla De Smedt, Mechelen (BE); Frederik Gelaude, Leuven (BE); Tim Clijmans, Heverlee (BE)

(73) Assignee: Materialise N.V., Leuven (BE)

( * ) Notice: Subject to any disclaimer, the term of this patent is extended or adjusted under 35 U.S.C. 154(b) by 380 days.

(21) Appl. No.: 13/379,966

(22) PCT Filed: Jul. 16, 2010

(86) PCT No.: PCT/EP2010/060350
§ 371 (c)(1),
(2), (4) Date: Mar. 12, 2012

(87) PCT Pub. No.: WO2011/007002
PCT Pub. Date: Jan. 20, 2011

(65) Prior Publication Data
US 2012/0165820 A1   Jun. 28, 2012

Related U.S. Application Data

(63) Continuation of application No. 12/505,237, filed on Jul. 17, 2009, now Pat. No. 8,414,591.

(30) Foreign Application Priority Data

Jul. 17, 2009   (GB) .................................. 0912431.4

(51) Int. Cl.
*A61B 17/58* (2006.01)
*A61B 17/60* (2006.01)
*A61F 2/00* (2006.01)
*A61B 17/17* (2006.01)
*A61B 19/00* (2006.01)

(52) U.S. Cl.
CPC .......... *A61B 17/175* (2013.01); *A61B 2019/505* (2013.01)
USPC ........................................................... 606/89

(58) Field of Classification Search
CPC ................................ A61B 17/175; A61F 2/32
USPC ........................................................... 606/89
See application file for complete search history.

(56) References Cited

U.S. PATENT DOCUMENTS 4,896,663 A * 1/1990 Vandewalls ..................... 606/79
5,514,141 A * 5/1996 Prizzi, Jr. ......................... 606/80
(Continued)

FOREIGN PATENT DOCUMENTS

EP   1 797 834 A1   6/2007
EP   1588668 B1   12/2008
(Continued)

OTHER PUBLICATIONS

PCT Notification Concerning Transmittal of International Preliminary Report on Patentability dated Jan. 17, 2012 for PCT Application No. PCT/EP2010/060350, 9 pages.
(Continued)

*Primary Examiner* — David Bates
*Assistant Examiner* — Samuel Hanna
(74) *Attorney, Agent, or Firm* — EIP US LLP

(57) ABSTRACT

The present invention provides surgical guiding tools for surgery on a bone head comprising a cutting component, a guiding component and a collar comprising a patient-specific component, which are interconnected and which ensure secure and accurate placement of the guiding tool and thus guarantee accurate implementation of the pre-operative planning of the surgical intervention.

12 Claims, 5 Drawing Sheets

(56) References Cited

U.S. PATENT DOCUMENTS

| | | | |
|---|---|---|---|
| 6,156,069 A * | 12/2000 | Amstutz | 623/22.11 |
| 2004/0236341 A1 | 11/2004 | Petersen | |
| 2005/0033290 A1* | 2/2005 | Nevelos et al. | 606/53 |
| 2005/0080426 A1* | 4/2005 | Qian | 606/96 |
| 2005/0113841 A1* | 5/2005 | Sheldon et al. | 606/88 |
| 2005/0245934 A1* | 11/2005 | Tuke et al. | 606/79 |
| 2005/0245936 A1* | 11/2005 | Tuke et al. | 606/89 |
| 2007/0162039 A1* | 7/2007 | Wozencroft | 606/89 |
| 2007/0233136 A1* | 10/2007 | Wozencroft | 606/86 |
| 2008/0033442 A1* | 2/2008 | Amiot et al. | 606/80 |
| 2008/0183179 A1* | 7/2008 | Siebel et al. | 606/89 |
| 2008/0234685 A1 | 9/2008 | Gjerde | |
| 2009/0118736 A1* | 5/2009 | Kreuzer | 606/96 |
| 2009/0254093 A1* | 10/2009 | White et al. | 606/89 |
| 2010/0016986 A1* | 1/2010 | Trabish | 623/23.14 |
| 2011/0015637 A1 | 1/2011 | De Smedt et al. | |
| 2011/0077650 A1* | 3/2011 | Braun et al. | 606/56 |

FOREIGN PATENT DOCUMENTS

| | | |
|---|---|---|
| EP | 1864617 B1 | 10/2009 |
| WO | 98/06359 A1 | 2/1998 |
| WO | 2005/110250 A1 | 11/2005 |
| WO | WO 2008/014618 A1 | 2/2008 |

OTHER PUBLICATIONS

The International Search Report dated Nov. 8, 2010 for PCT Application No. PCT/EP2010/060350.

* cited by examiner

SURGICAL GUIDING TOOL, METHODS FOR MANUFACTURE AND USES THEREOF

CROSS-REFERENCE TO RELATED APPLICATIONS

This application is U.S. National phase of PCT Application No. PCT/EP2010/060350, filed Jul. 16, 2010, which claims priority to European Application No. 09124314, filed Jul. 17, 2009 and U.S. application Ser. No. 12/505,237, filed Jul. 17, 2009.

FIELD OF THE INVENTION

The present invention relates to surgical guiding tools which are of use during limb bone surgery, more specifically during limb bone resurfacing surgery for guiding a surgical instrument. The present invention further relates to methods for manufacturing these tools and specific methods for using the surgical guiding tools of the invention in limb bone resurfacing surgery.

BACKGROUND

One of the options in the treatment of advance joint arthrosis is joint resurfacing, i.e. removing only the diseased or damaged surfaces of the head of the bone. In the United States, hip resurfacing was first approved by the FDA based on the Birmingham Hip Resurfacing (BHR) technology developed by Derek McMinn. The BHR has a mushroom shape with a metal cap for placement on the femur head which fits into a cup placed in the acetabulum. The cap is fixed onto the head of the femur by way of a very small stem which is introduced through the femur head (and neck)

Hip resurfacing or hip surface replacement has a number of advantages over classical hip replacement therapy. The main advantage of the bone conserving system of hip resurfacing is that femoral head and femoral canal can be preserved such that when a revision is required, there is still a complete femur bone left for a stem in case total replacement becomes necessary. Moreover, there is more chance that the natural gait is recovered and the stress is transferred in a natural way through the neck of the femur rather than immediately on the thigh (which often causes pain). Finally, as resurfacing devices can be made in metal or other wear-resistant material, the resurfaced hip has a low wear rate such that even a young patient will probably not outlive the implant. In most cases, bone head resurfacing will be preferable over procedures which involve total bone head replacement.

The satisfactory performance of a joint surface replacement device is determined not only by the design of the device itself, but also by the surgical positioning of the implanted component(s) and the proper fixation of the implant. Improper placement or positioning of the implant will not only result in a failure to restore the clinical bio-mechanics of the joint but will result in inadequate fixation of the implant to the bone. To ensure the correct installation of a new surface on the head with resurfacing device use is made of guiding tools which can ensure the appropriate position and orientation of cutting, drilling and preparation tools based on pre-operative planning of the surgical intervention.

A number of different alignment devices have been described in the art.

U.S. Pat. No. 4,860,735 discloses a drill alignment apparatus which is mounted on top of a drill handle and comprises an alignment rod and a clamp apparatus for fixing onto the bone. By placing the clamp on the bone, the drill handle can be moved only in the direction of the alignment rod. U.S. Pat. No. 5,312,409 discloses a drill alignment guide, which comprises a adjustable clamp assembly for clamping onto the bone connected by an L-shaped bar to a drill guide. Upon clamping of the device on the bone, the drill guide is positioned on the bone head. U.S. Pat. No. 4,896,663 discloses a femoral drill jig comprising a clamping mechanism which clamps on to the femoral neck and a head cone which comprising a guide bushing for guiding a drill into the femur head. Similarly, EP1588688 discloses an alignment guide for use in femoral surgery with either an arm or a moveable c-ring for fixing around the neck of the femur.

The above-described methods involve generic, adjustable devices that consist of a guiding element, an element that clasps around a part of the bone, and one or more arms connecting the two. These devices are often unstable as they do not fit perfectly on the patient's bone and in some cases inaccurate because of the great distance between the supporting anatomy and the planned point of entry of the surgical instrument. Indeed, as a large part of the head of a limb bone is covered with cartilage, this surface is smooth and slippery which makes it less suitable as secure attachment point. In addition, the thickness of the cartilage may vary from patient to patient. Cartilage is very difficult to segment on CT-images and even using MRI implies an additional step which is time-consuming. Thus it is very difficult to design structures precisely fitting on to the bone head.

In addition, the prior art devices such as those referred to above are all quite bulky, mainly due to the presence of extended support arms and thus require the availability of a large surgical window.

An increasing number of surgical interventions currently benefit from the use of medical-image-based models which can assist in precisely executing the pre-operative planning of the intervention. U.S. Pat. No. 5,768,134 describes methods for making a medical model using rapid prototyping which model can includes artificial elements which can be functional such as drill-guides or pins.

There is a need for surgical guides, which do not require excessive image analysis and are not bulky but nevertheless are stable and provide the ability to accurately and efficiently insert or contact a surgical instrument into or with the head of a patient's limb bone.

SUMMARY OF THE INVENTION

The present invention relates to patient-specific surgical guiding tools for a bone head which can be generated based on a CT scan (i.e. without requiring segmentation of the cartilage) and nevertheless provide stable and accurate guidance of the surgical instrument. Moreover, as the tool ensures a direct fit in the desired position, no alignment is necessary upon, which saves time during placement.

In a first aspect, the present invention provides patient-specific surgical guiding tools for a head of a limb bone comprising a guiding component, a cutting component, a collar for placing on the bone neck and a connecting structure.

More specifically, the present invention relates to patient-specific surgical guiding tools for a head of a major limb bone comprising (i) a guiding component for guiding a surgical instrument, (ii) a cutting component comprising one or more cutting elements, positioned so as to cut in the cartilage of the head of the bone upon placement of the surgical guiding tool on the bone head, (iii) a collar spanning at least a part of the contour of the neck of the bone but retaining an opening which allows passage of the neck at least its smallest diameter and comprising a patient-specific component, and (iv) a connecting structure connecting said collar to said cutting component and/or to said guiding component, such that said collar, said cutting component and said guiding component are interconnected. The guiding tools according to the invention are further characterized in that the connecting structure forms at least one aperture allowing the passage of the bone head and ensuring placement of the guiding component on the bone head upon placement of the collar on the bone neck, and in that the cutting component is positioned at both sides of said at least one aperture and at a maximal angle of 90° from the interior bisector of the angle formed by the lines connecting the edges of the aperture and the central axis of the head of the bone upon placement of the surgical guiding tool on the bone head. In particular embodiments, the cutting component comprises at least two cutting elements and the cutting elements are positioned each at a different side of said at least one aperture and at a maximal angle of 90° from the interior bisector of said angle.

In particular embodiments, the edges of said cutting elements are all positioned in the same plane. More particularly, the edges of said cutting elements are positioned in a plane perpendicular to the position of the central axis of the head of the bone upon placement of the surgical guiding tool on the bone head. Accordingly, in the guiding tools according to the present invention, the cutting component is used to ensure a secure fit onto the bone head and cut transversally into the surface (cartilage) of the bone head. This is different from tools used in the preparation and shaping of the outer bone head surface (e.g. hip resurfacing) by cutting away the surface of the bone head symmetrically around an axis, which is achieved by cutting elements which run in parallel with the central axis of the head of the bone (such as in EP1864617).

In particular embodiments of the invention, surgical guiding tools are provided wherein the cutting component is positioned at both sides of said at least one aperture and at a maximal angle of 90° from the interior bisector of the angle formed by the lines connecting the edges of the aperture and the central axis of the head of the bone upon placement of the surgical guiding tool on the bone head. In particular embodiments, the cutting component comprises at least two cutting elements and at least two of the two or more cutting elements are positioned each at a different side of the aperture and each at an angle of about 75° from the interior bisector of the angle formed by the lines connecting the edges of the aperture and the central axis of the head of the bone. In further particular embodiments, at least two of the two or more cutting elements are positioned each at a different side of the aperture and each at an angle of 80° from the interior bisector of the angle formed by the lines connecting the edges of the aperture and the central axis of the head of the bone.

In particular embodiments of the surgical guiding tools described herein, the two or more cutting elements are interconnected by one or more ring structures spanning the contour of the bone head by at least 180°.

In further particular embodiments of the surgical guiding tools of the invention, the central axis of the guiding component is positioned in or in the extension of the central axis of the head of the bone upon placement of the surgical guiding tool on the bone head. More particularly, the guiding component is positioned perpendicular to the plane formed by the edges of the one or more cutting elements.

In particular embodiments, the guiding tools according to the invention comprise a collar which spans the contour of the neck of the bone head over about 180°. Alternatively, the collar may span the contour of the neck over more than 180°. In most particular embodiments, for placement on a neck of a bone head which is ellipsoid, the guiding tool may comprise a collar which spans the bone neck over more than 180° and wherein the plane formed by the collar contains a longitudinal axis and the opening of the collar is positioned such that the axis connecting the ends of the opening is not perpendicular to the longitudinal axis of the plane formed by the collar. More particularly, the opening may be positioned such that it is parallel with the longitudinal axis of the plane formed by the collar.

In particular embodiments, the devices of the present invention comprise at least one component which is made by additive manufacturing. This allows the integration of a patient-specific component which further increases the accuracy of the guiding tools. Indeed, the guiding tools of the prior art are typically standard tools which can at most be adjusted mechanically to fit every patient, but do not ensure the patient-specific fit and accuracy.

In a second aspect, the present invention relates to methods for using the tools of the present invention, more particularly methods for placing the guiding tools of the invention on a bone head, and most particularly, methods for introducing a surgical instrument into a head of a limb bone, which comprise placing the tools of the invention on the bone head.

In a first embodiment, the present invention relates to methods for introducing a surgical instrument into a head of a major limb bone of a patient, which methods comprise: (a) providing a surgical guiding tool as described hereinabove, whereby the tools are provided such that the patient-specific component of the collar is made complementary to a surface of the bone neck of the patient and the guiding component is designed to guide the surgical instrument in a predefined trajectory (determined by pre-operative planning); and (b) securing the surgical guiding tool on the bone head. The latter can be done either by direct placement or by rotation placement. In particular embodiments, rotation placement of the guiding tool is envisaged, which involves:

positioning the surgical guiding tool with the opening of the collar facing the bone neck such that the patient specific component of the collar is aligned at an angle with its complementary surface on the bone neck, moving the surgical guiding tool over the bone head such that the central axis of the bone head or neck is perpendicular to the direction of the movement until the tool is positioned over the bone head and neck, rotating the surgical guiding tool to align the collar with the neck of the bone such that the patient-specific component of the collar locks into the complementary surface of the neck of the bone, thereby applying pressure on the cutting elements that are positioned at opposite sides of the aperture so as to cut a groove in the cartilage of the bone head; and (c) introducing the surgical instrument through the guiding component.

While the devices according to the invention can generally be used for either direct placement or rotational placement, particular features may render the device either particularly or exclusively suited for rotation/direct placement. More particularly, where the neck of the bone head is ellipsoid and the opening of the collar of the guiding tool according to the invention spans an angle of less than 180° and is not perpendicular to the longitudinal axis of the ellipsoid collar, direct placement may not be possible.

Accordingly, the invention provides methods for introducing a surgical instrument into a head of a major limb bone which comprises a neck which is ellipsoid, which method comprises: (a) providing a surgical guiding tool, whereby the guiding tool comprises a collar which spans the bone neck over more than 180° and wherein the plane formed by the collar contains a longitudinal axis and the opening of the collar is positioned such that the axis connecting the ends of the opening is not perpendicular to the longitudinal axis of the plane formed by the collar, and whereby:

the patient-specific component is made complementary to a surface of the bone neck of the patient and the guiding component is designed to guide said surgical instrument in a predefined trajectory; and (b) securing the surgical guiding tool on the bone head and neck by introducing the smallest diameter of the bone neck through the opening of the collar and placing the surgical guiding tool over the bone head; and rotating the surgical guiding tool to align the collar with the neck of the bone such that the patient-specific component of the collar locks into the complementary surface of the neck of the bone, thereby applying pressure on the cutting elements that are positioned at opposite sides of the aperture so as to cut a groove in the cartilage of the bone head; and (c) introducing the surgical instrument through the guiding component.

In further embodiments, the invention provides methods which involve direct placement of a guiding tool according to the invention. More particularly, the invention provides methods for introducing a surgical instrument into a head of a major limb bone, which methods comprise (a) providing a surgical guiding tool as described herein, whereby the collar of the tool allows direct placement of the tool on the neck of the bone head and whereby:

the patient-specific component is made complementary to a surface of the bone neck of the patient and the guiding component is designed to guide said surgical instrument in a predefined trajectory; and the method further comprises (b) securing the surgical guiding tool on the bone head and neck by positioning the surgical guiding tool with the opening of the collar facing the bone neck such that the patient specific component of the collar is aligned in parallel with its complementary surface on the bone neck, and moving the surgical guiding tool over the bone head such that the central axis of the bone head or neck is perpendicular to the direction of the movement until the patient-specific component of the collar locks into the complementary surface of the neck of the bone, thereby applying pressure to said cutting elements that are positioned at opposite sides of the aperture so as to cut a groove in the cartilage of the bone head; the method further comprising (c) introducing the surgical instrument through the guiding component.

More particularly, the methods described hereinabove are methods for transferring a pre-planned intervention in the bone head to surgery.

In a further aspect, the present invention provides methods for manufacturing a patient-specific surgical guiding tool for a surgical intervention on a head of a limb bone according to the invention.

In particular, the invention provides methods for manufacturing a patient-specific surgical guiding tool comprising a cutting component with cutting elements, a collar, a guiding component and a connecting structure and further characterized by the features described herein, which methods comprise (a) obtaining volume information of the bone head and neck, (b) identifying and selecting one or more parts of the bone neck, which contain sufficient features to be patient-specific, (c) determining the appropriate position of the guiding component with regard to the bone head, based on the pre-operative planning of the desired path of the surgical tool in the bone head; and (d) preparing the surgical guiding tool wherein:

(i) the position of the connecting structure, the cutting component and the collar is determined based on the image of the bone head and neck obtained in step (a)

(ii) the collar comprises a patient-specific component comprising at least one patient-specific area based on the patient-specific parts of the neck identified in step (b) and (iii) the guiding component is positioned in the surgical guiding tool such that, upon placement of the guiding tool on the bone head and neck, the guiding component is positioned as determined in step (c).

BRIEF DESCRIPTION OF THE FIGURES

The following description of the figures of specific embodiments of the invention is merely exemplary in nature and is not intended to limit the present teachings, their application or uses. Throughout the drawings, corresponding reference numerals indicate like or corresponding parts and features.

DETAILED DESCRIPTION

Figure 1:
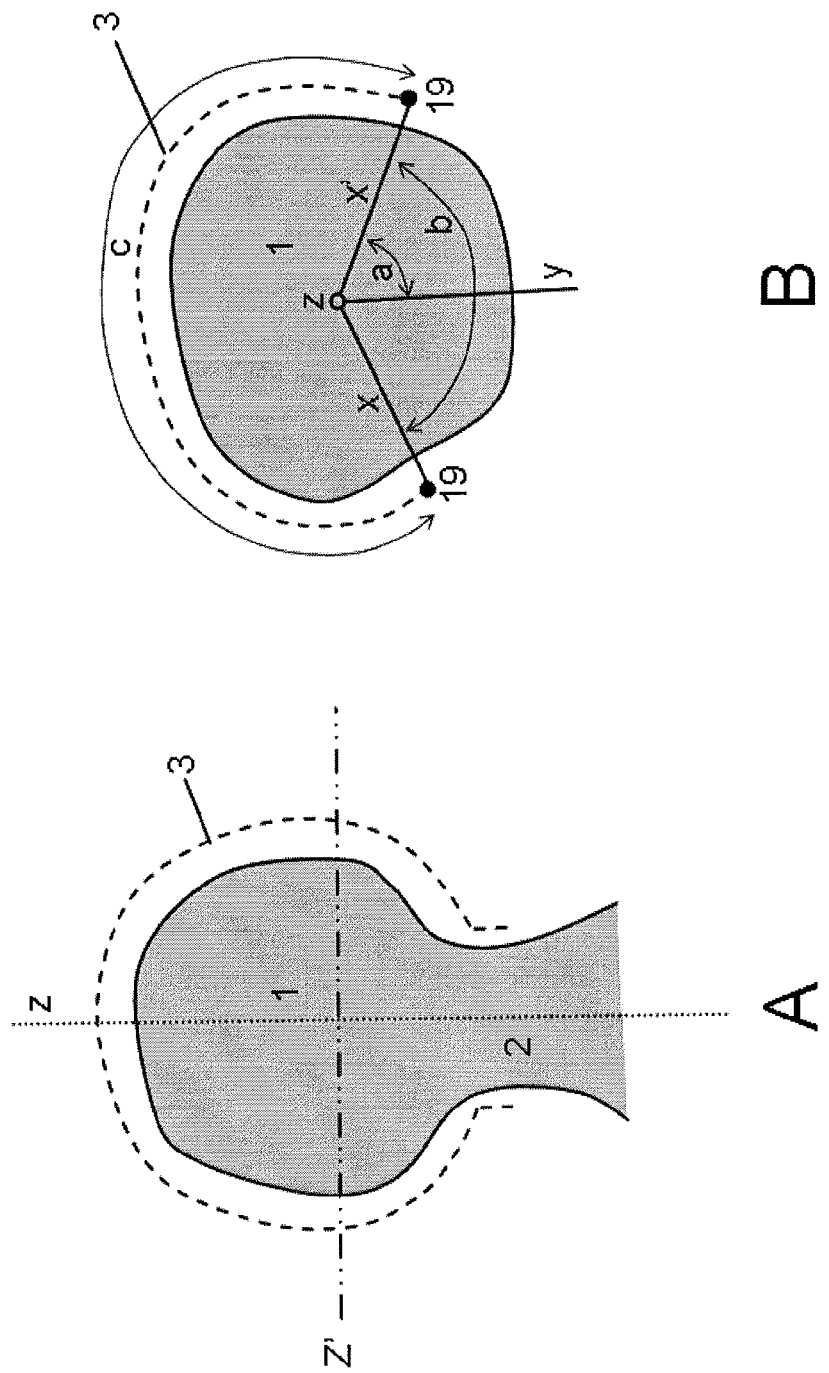
FIG. 1A: Schematic drawing of a bone head (1) and neck (2) when placed into a guiding tool (3) according to the present invention. Plane Z' intersects the bone head at its largest width. Axis z corresponds to the central axis of the bone head.
FIG. 1B: Cross-sectional view of the bone head (1) (resulting from the intersection with plane Z') when placed into a guiding tool (3) according to a specific embodiment of the present invention. Axis z is perpendicular to the cross-sectional plane and corresponds to the central axis of the bone head. Axis y corresponds to the interior bisector of the angle formed by the lines connecting the edges of the aperture and the central axis of the head of the bone. Axes x and x' correspond to the lines connecting the edges of the aperture. Angle b is the angle formed by the lines connecting the edges of the aperture and the central axis of the head of the bone. Angle a is the angle formed by the interior bisector of angle b and one of the lines connecting the edges of the aperture. Angle c corresponds to the angle by which the bone neck is spanned by the cutting component.

The present invention will be described with respect to particular embodiments but the invention is not limited thereto but only by the claims. Any reference signs in the claims shall not be construed as limiting the scope.

Where the term "comprising" is used in the present description and claims, it does not exclude other elements or steps. Where an indefinite or definite article is used when referring to a singular noun e.g. "a" or "an", "the", this includes a plural of that noun unless something else is specifically stated.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The terms or definitions used herein are provided solely to aid in the understanding of the invention.

The present invention provides patient-specific surgical guiding tools which allow accurate and stable introduction of a surgical instrument into the head of a limb bone. More particularly, the invention provides medical-image-based patient-specific surgical guiding tools providing the ability to accurately insert a surgical instrument into the head of a patient's limb bone according to a predefined planning without the need for segmentation of the cartilage of the head.

Surgical guiding tools according to the present invention at least comprise a guiding component, a cutting component, a collar for placement on the bone neck and a connecting structure. The different components of the guiding tools according to the present invention are described more in detail hereafter. Unless specified (e.g. in the context of placement of the tools of the invention), reference to the position of the head and/or neck of the bone is intended to refer to the position of the head and/or neck of the bone, respectively, when the tool has been placed onto the bone head and neck.

According to the present invention, optimal accuracy of a surgical intervention is ensured by using a surgical guiding tool comprising a combination of a cutting component comprising a cutting element, more particularly two or more cutting elements, which cut into the cartilage on the bone head, and a collar, comprising a patient-specific component which fits onto at least a section of the bone neck, which ensures a specific fit of the tool in a predetermined position. Accordingly, the surgical guiding tools of the invention typically fit over at least part of the bone head and neck, with the aim of accurately and stably positioning a guiding component which ensures guidance of a surgical instrument typically (but not necessarily exclusively) into the upper half of the bone head.

In the present description of the guiding tools of the invention, reference is made to angles to define the extent to which the guiding tool structures spans the contour of the head of the bone and the neck (or collar) of the bone head (circumference angle). Similarly, the guiding tool structures contain an aperture and an opening for passage of the bone head and neck (or collar) or a part thereof, respectively. The aperture and opening of the guiding tool are defined by an angle which is typically complementary to the circumference angle (e.g. 360-circumference angle of the connecting structure spanning contour of the bone head=angle of the aperture). It will be understood to the skilled person, that in general, while a difference of 10° on these angles may have a functional impact on the guiding tool, limited variations of the angles around the indicated values will not significantly impact the function of the structures of the guiding tool and can be considered as obvious alternatives of the values provided. Accordingly, where referring to an angle in the context of the present invention, unless specified, typically variations of +/−5° should be considered as equally envisaged. Similarly, in some embodiments variations of +10° or −10° may also be envisaged. At the same time, it will be understood by the skilled person that, where reference is made to an angle of more or less than 180°, the cut-off is effectively 180° as this will impact the functionality of the relevant structure of the tool.

The surgical guiding tools according to the present invention comprise a cutting component. The purpose of the cutting component is to cut into the cartilage of the head of the bone, thereby fixing the tool tightly onto the bone head upon placement. A large part of the head of a limb bone is covered with cartilage. This cartilage tissue has a thickness that varies from patient to patient. Designing a tool which fits precisely over this cartilage layer would requires segmentation of the cartilage layer for every patient. Segmentation of cartilage is very difficult from CT-images and even when using MRI implies an additional time-consuming step. The cartilage moreover provides a surface which is smooth and slippery. The cutting component present in a guiding tool according to the invention not only ensures fixation irrespective of the thickness of the cartilage layer but provides sufficient grip and support upon placement of the guiding tool on the bone head such that a surgical instrument can be inserted in an accurate and stable manner.

The cutting component of the guiding tools according to the invention comprises two or more cutting elements. The number of cutting elements in the cutting component of the tools according to the present invention may vary. In particular embodiments the number of cutting elements is at least two. For example, the number of cutting elements in the cutting component may be two, three, four, five, six, seven, eight or more. Typically, where more than two cutting elements are provided, these elements are positioned along the contour of the inside of the surgical guiding tool such that they cut at different positions along the contour of the bone head when the tool is placed on the bone head. In further particular embodiments, the two or more cutting elements are joined together to form one continuous cutting edge, more particularly spanning the contour of bone head when positioned in the guiding tool.

The cutting elements (also referred to herein as knife contacts) each have a shape which, upon placement of the guiding tool on the bone head, cuts into the cartilage. The shape of the cutting elements is not critical. Typically, the cutting elements have a sharp point or a sharp edge from which they taper outward, i.e. in a direction away from the central axis of the head of the bone (or part thereof), when positioned inside the guiding tool. More particularly, the sharp edge or point of the cutting elements is directed perpendicular to the bone surface. In particular embodiments the edge of the cutting elements is directed towards the central axis of the bone head when the tool is positioned thereon. The length of the sharp edges of the cutting elements may vary. Typically, the length of the sharp edge of the cutting elements is between 5 mm and 30 mm more particularly between 10 and 20 mm, most particularly between 15 and 18 mm. In particular embodiments, the different cutting elements, positioned so as to span the contour of the bone head, are interspaced by at least 2 mm, more particularly by at least 4 mm, most particularly by about 10 mm. The sharp edge of the cutting elements may be smooth or be serrated.

When considering the position of the cutting elements in the tool, the edges of the two or more cutting elements may lie in the same plane or in one or more different planes. When the bone head is positioned in the guiding tool, this plane makes a cross-section of the bone head. Where the edges of the two or more cutting elements are positioned in the same plane, this makes it possible to exert more pressure on the cutting elements upon placement. More particularly, the edges of two or more of the cutting elements are located in the same plane and at opposing sides of the aperture of the tool.

In particular embodiments, the edges of the two or more cutting elements are located in the same plane and this plane forms an angle with the position of the central axis of the surgical guiding tool and/or the central axis of the bone head upon placement of the surgical guiding tool on the bone head. In further particular embodiments, this plane is perpendicular to the position of the central axis of the surgical guiding tool and/or the central axis of the head of the bone upon placement of the surgical guiding tool on the bone head. In particular embodiments, this plane makes a cross-section of the bone head when placed in the tool at a level where the bone head and the aperture of the tool are the widest. Preferably, the positioning of the cutting elements ensures that the pressure applied to the guiding tool upon introduction and working of the surgical instrument is perpendicular to the direction of the clasp function ensured by the cutting elements. In particular embodiments, a guiding tool is provided wherein the edges of the cutting elements are positioned in one plane corresponding to the cross-section of the bone head and perpendicular to the longitudinal axis of the bone head, in particular embodiments, at its largest width. Typically, where this cross-section of the bone head is essentially circular, the sharp points or the sharp edges of the cutting elements are directed towards the central axis of the bone head when positioned in the guiding tool which, in particular embodiments corresponds to the central axis of the guiding tool.

In particular embodiments, which will be described below, typically where this cross-section of the bone head is essentially circular, the guiding tool can be configured such that (at least some) rotation of the guiding tool on the bone head is possible and will result in the cutting elements cutting a groove in the cartilage layer (as described more in detail below).

According to the invention, the cutting elements are positioned in the guiding tool structure such that, upon placement of the tool on the bone head, they cut in the cartilage of the bone head. This cutting implies that the cutting elements go through at least a certain portion, layer or thickness of the cartilage of the bone head, upon placement of the guiding tool on the bone head. Based on 3D volume information as reconstructed e.g. from digital CT or an MRI scan of a bone head, the outline of the head can be measured and the position of the cutting elements can be determined such that the edge of the cutting elements maintains a minimal distance from the bone of the bone head. Depending on the envisaged position of the cutting elements from the bone of the bone head and the thickness of the cartilage the two or more cutting elements may cut through a portion, layer or thickness of cartilage, which may vary from 0.1 to 3.0 mm. Accordingly, in certain embodiments, the cutting elements may cut through a portion, layer or thickness of the cartilage of the bone head without contacting or supporting on the underlying bone structure. However, according to particular embodiments, the cutting elements may cut completely through the full thickness of the cartilage of the bone head each contacting and/or supporting on the underlying bone structure upon placement of the surgical guiding tool on the bone head.

The cutting elements of the guiding component are supported by one or more member(s) which are part of the connecting structure of the guiding tool. The connection between the members and the rest of the connecting structure ensure a secure fit of the entire guiding tool of the invention onto the bone, by way of the cutting element. This allows for a more compact structure than traditional guiding devices which require bulky support arms. As will be detailed below, the connecting structure of the guiding tool is configured so as to ensure a cavity (such that the guiding tool fits over at least part of the bone head) and at least one aperture (allowing the passage of the bone head into the cavity of the tool). More particularly, the aperture in the guiding tool of the invention allows the passage of the bone head upon lateral placement of the guiding tool on the bone head. Typically, the guiding tool is placed laterally on the bone head and neck and the dimensions of the aperture of the connecting structure corresponds to a longitudinal section of the bone head or the part thereof on which the guiding tool is to be placed. It will be understood that, irrespective of further extensions of the connecting structure which are exterior to the structure which forms the contour of the bone head, the "edges" of the connecting structure forming the aperture (i.e. opening allowing passage of the bone head) correspond to "edges of the aperture". The lines connecting the edges of the aperture at its widest point and the central axis of the guiding tool and/or the (part of) the bone head when placed in the guiding tool form an angle. This angle can be used to measure the size of the aperture. Similarly, the interior bisector of this angle (i.e. the line which runs from the central axis of the guiding tool (or bone head therein) through the middle of the aperture at its widest point), herein referred to as the "interior bisector of the aperture" can be taken as a reference to describe the position of the cutting elements in the guiding tool.

FIG. 1 shows a schematic drawing (A) of a femoral head (1) and neck (2) as well as a cross-sectional view (B) of the femoral head (1) when placed into a guiding tool (3) according to the present invention. In FIG. 1B the interior bisector of the aperture is indicated with the letter "y". FIG. 1 illustrates an embodiment wherein the lines connecting the edges (19) of the aperture at its widest point and the central axis of the bone head (z) when placed in the guiding tool form an angle (b). This angle (b) can be used to describe the size of the aperture. Similarly, the interior bisector (y) of this angle (b) can be taken as a reference to describe the position of the cutting elements in the guiding tool. In this particular embodiment illustrated in FIG. 1, the aperture of the guiding tool spans an angle (b) of 140° to 160° of the contour of the bone head, to allow passage of the bone.

As detailed herein, the cutting component may comprise one, or more particularly two or more cutting elements. When the cutting component comprises two or more cutting elements, two of these two or more cutting elements are positioned within the guiding tool such that at opposing sides of the aperture and each at a maximal angle of 90° from the interior bisector of the angle formed by the lines connecting the edges of the aperture and the central axis of the head of the bone upon placement of the surgical guiding tool on the bone head ("outer" cutting elements). The two outer cutting elements will contact the bone head first, when the tool is placed on the bone head and will make a groove in the cartilage of the bone head. When the cutting component comprises only one cutting element, this element spans the circumference of the bone head, from one end of the aperture to the other (excluding the aperture itself).

Figure 2:
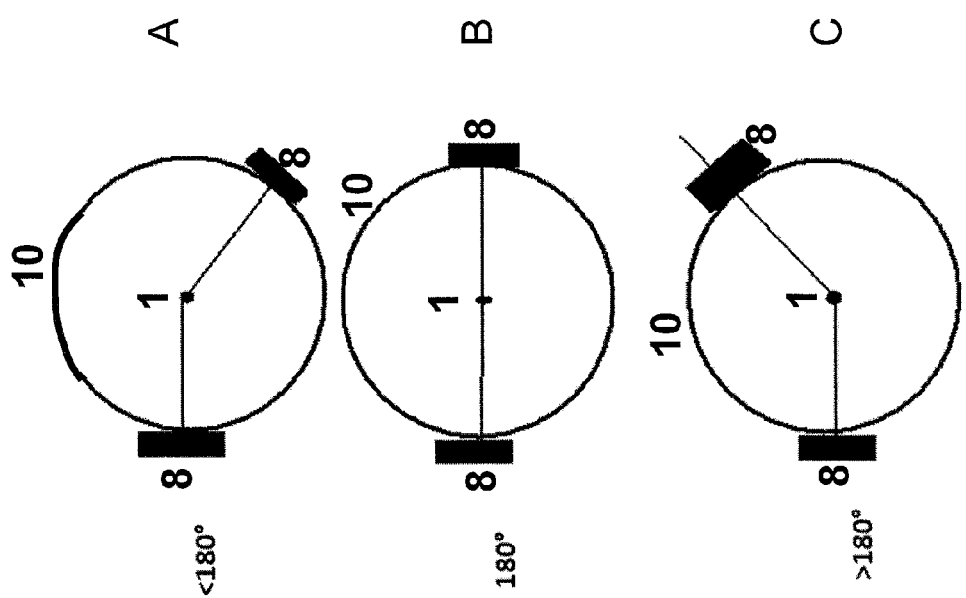
FIGS. 2A, 2B and 2C: Cross-sectional views of the bone head (1) when placed into a guiding tool according to three particular embodiments of the present invention. A: At least two cutting elements (8) are positioned such that the bone head is spanned by an angle of less than 180°. The aperture (10) accordingly spans the bone head an angle of more than 180°. B: At least two cutting elements (8) are positioned such that the bone head is spanned by an angle of about 180°. The aperture (10) accordingly spans the bone head an angle of about 180°. C: At least two cutting elements (8) are positioned such that the bone head is spanned by an angle of more than 180°. The aperture (10) accordingly spans the bone head an angle of less than 180°.

The position of these one or more cutting elements is defined at the edges which form the aperture, as these edges of the cutting elements, together with their supporting structure, define the aperture. This is illustrated schematically in FIG. 2. The positioning of the outer cutting elements at about a 90° angle or less from the interior bisector of the opening is important as, if they would be positioned at more than 90° from the interior bisector of the aperture, the cutting component would not provide the desired stability (FIG. 2A). Accordingly, the one or more cutting elements should be positioned such that they include the presence of cutting elements close to the edges of the aperture. More particularly, a cutting element should be present on each side at about 90° of the interior bisector of the aperture (FIG. 2B), or less, more particularly at an angle which is between 90 and 70° of the interior bisector of the aperture (FIG. 2C).

Typically, as detailed above, cutting elements are placed at opposing sides at the edges of the aperture. These are referred to as the "outer" cutting elements. As detailed above, the cutting component may also be one cutting element which spans from one outer cutting element to the other (excluding the aperture). More particularly, tools are provided wherein the outer cutting elements are positioned at the edges of the aperture at a level corresponding to the position of the widest diameter of the bone head. This ensures (a) that the outer cutting elements start cutting into the cartilage upon first contact of the guiding tool with the bone head and (b) that optimal pressure can be applied on the cutting elements when placing the tool onto the bone head. For instance, the outer cutting elements can be positioned each at a different side of the aperture and each at a maximal angle of between 70° and 80° or between 80° and 90° from the interior bisector of the aperture. Accordingly, in particular embodiments, the aperture of the guiding tool at its widest point spans about 140° to 180° of the contour of the bone head, to allow passage of the bone head and two of the cutting components are placed at the outer edges of this aperture. Where the width of the aperture of the guiding tool corresponds to the diameter of the bone head (i.e. where the aperture spans about 180° of the contour), two cutting elements of the tool will be positioned in the cartilage at opposite sides of the bone head upon placement of the tool on the bone head. It will be understood that the guiding tool may contain cutting elements located in several planes, where in the additional planes the cutting elements may or may not contain outer cutting elements (i.e. located at the edge of the aperture).

In certain particular embodiments, at least two of the two or more cutting elements are positioned each at a different side of the aperture (the "outer" cutting elements) and each at an angle of about 80° from the interior bisector of the aperture (angle "a" of FIG. 1B, where angle "a" is about 80°). Similarly, the cutting component where it comprises one cutting element may span a c-ring with an opening of about 160° (i.e. leaving an aperture which spans about 80° from the interior bisector of the aperture) Accordingly, in these embodiments, the aperture spans about 160° of the contour of the bone head when placed in the guiding tool (angle "b" in FIG. 1B, where angle "b" is about 160°). This position of the cutting elements is optimal for direct placement of the surgical tool. As will be detailed below, this ensures an overhang of the edges of the aperture when placed on the bone head (accordingly forming an "undercut") whereby the bone head is clasped into the guiding tool. As the material of the guiding tools according to the invention is typically material which has some flexibility, upon placement of the tool on the bone head, pressure is placed on the cutting elements, which ensures the cutting of the elements through the cartilage and opening of the aperture allowing passage of the bone head.

In further particular embodiments, at least two of the two or more cutting elements are positioned each at a different side of the aperture and each at an angle of about 75° from the interior bisector of the aperture (angle "a" in FIG. 1B is about 75°). Or, where the cutting component comprises one cutting element it corresponds to a structure comprising cutting elements in these positions. Accordingly, in these embodiments, the aperture spans about 150° of the contour of the bone head when placed in the guiding tool (angle "a" in FIG. 1B is about 150°). This position of the cutting elements is optimal for use in a tool which is designed for rotation placement (see below).

Where the cutting component comprises more than two cutting elements, the position of the additional cutting elements is less critical. Typically, the additional cutting elements are positioned in the same plane at more than 90° from the interior bisector of the aperture. In particular embodiments of the invention, a guiding tool is provided which is rotated into position after placement on the bone head (see below). In these embodiments, the device may be rotated such that the additional cutting elements slide into the groove formed by the "outer" cutting elements in the cartilage upon placement of the device.

The members supporting the one or more cutting elements in the tools according to the invention can be of different shapes and/or sizes. According to certain embodiments, the cutting elements are supported and interconnected by one or more structures such as but not limited to ring structures, which are positioned such as to span at least part of the contour of the bone head, however leaving a clearance of about 3 to 10 mm, typically of about 5 mm, with the bony surface of the bone head. More particularly, where there are two or more cutting elements, these are interconnected by a structure such as a ring structure which spans the contour of the head of the bone by at least 180°. In specific embodiments, one or more structures together span the contour of the bone head by more than 180° (angle "c" in FIG. 1B, where angle "c" is more than 180°). According to these embodiments, an overhang of the ends of the ring structures is created when the guiding tool is placed on the bone head (forming an "undercut"). Of course, it will be clear to the skilled person that the one or more connecting structures, including those which support the cutting component must retain an aperture which (taking into account the resilience of the material) allows passage of the bone head. Accordingly, the minimal size of the aperture will be dependent on the type of material used. In particular embodiments, the size of the aperture formed by the connecting structure and the cutting elements is configured such that, when it is pushed onto the bone head, the cutting elements cut transversally into the cartilage of the bone head, while they do not or barely cut into the bone of the bone head. As a result of the overhang, the surgical guiding tool upon placement on the bone head snaps into place and remains locked in position. The bone head is thereby clasped into the guiding tool by the cutting elements positioned on the one or more ring structures.

In particular embodiments, the one or more ring structures together span the contour of the bone head by between 180° and 220° (angle "c" in FIG. 1B, where angle c is between 180° and 220°). In further particular embodiments the one or more ring structures together span the contour of the head of the bone by at least 200° (see FIG. 1B, where angle c is about 200°), maintaining an aperture of 160° (FIG. 1B, where angle b is about 160°). According to further particular embodiments, the one or more ring structures together span the contour of the head of the bone by about 210° (see FIG. 1B, where angle c is about 210°), maintaining an aperture of 150° (see FIG. 1B, where angle b is about 150°).

In the surgical guiding tool according to the invention, the connecting structure further supports the guiding component. This aspect of the connecting structure is discussed more in detail below in the context of the guiding component.

The surgical guiding tools of the present invention further comprise a collar for placement on the neck of the bone head. The collar of the surgical guiding tools according to the present invention ensures the correct placement of the guiding tool on the patient's bone. It consists of one or more parts and comprises a patient-specific component. Accordingly, the collar of the guiding tools of the invention comprises a patient-specific component comprising one or more patient-specific areas and optionally comprises one or more non-patient specific areas. A patient-specific area is an area on the inside of the collar which interlocks with the neck of the bone on which the tool is to be placed in a patient-specific way. Typically, a patient-specific area is a surface that is fully complementary to a surface on the neck of the bone head. In particular embodiments this complementarity taking into account a clearance between the guide tool surface and the patient's bone of between 0.1-0.2 mm. The one or more patient-specific areas are positioned on the inside of the collar such that they can be contacted with/positioned opposite to the corresponding surface of the neck of the bone head upon placement of the guiding tool. When a patient-specific area of the collar is contacted with/positioned opposite to its corresponding complementary part of the surface of the neck of the bone head, the two surfaces interlock, fixing the collar (and thus the guiding tool) into a predetermined position.

Thus, the guiding tools according to the present invention comprise at least one patient-specific area, which is typically a patient-specific surface that is designed to fit onto at least part of the bony neck area of a patient's limb bone and that is fully complementary to sufficient features of that part of the bone neck to determine a unique locking position. Typically, a patient-specific surface is selected based on anatomical features present on the neck. However it can be envisioned that in particular embodiments features are introduced into the neck of the patient's bone to allow the generation of patient-specific area based thereon.

The size of the one or more patient-specific areas of the collar of the guiding tools of the present invention is not critical. Depending on the embodiment they can span all or part of the inside of the collar.

The location of the one or more patient-specific areas in the collar is not critical and may be spread out over one or more parts of the collar see below. However, the position of the corresponding surface on the bone neck will determine its position in the collar of the guiding tool. Indeed, the patient-specific areas must be place such that, upon interlocking of the patient-specific area with its corresponding surface in the neck of the bone, the surgical guidance tool is in the desired position.

As indicated above, the collar of the guiding tools according to the present invention can comprise one or more parts. Where the collar comprises more than one part, these parts can be directly or indirectly interconnected through a connecting structure. As detailed above, one or more of the parts of the collar may comprise a patient-specific area.

Figure 3:
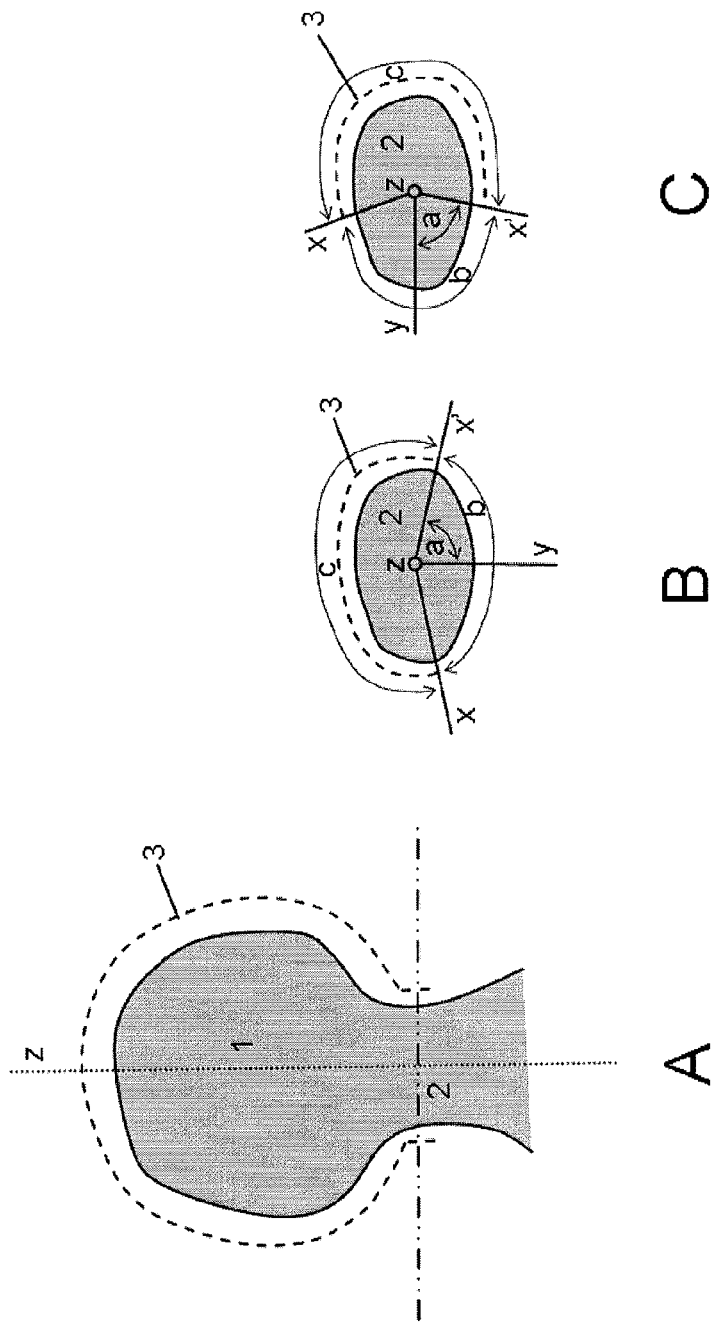
FIG. 3A: Schematic drawing of a bone head (1) and neck (2) when placed into a guiding tool (3) according to the present invention. Plane Z' intersects the bone neck. Axis z corresponds to the central axis of the bone head.
FIGS. 3B and 3C: Cross-sectional views of the bone neck (2) (resulting from the intersection with plane Z') when placed into a guiding tool (3) according to two particular embodiments of the present invention. Axis z is perpendicular to the cross-sectional plane and corresponds to the central axis of the bone head. Axis y corresponds to the interior bisector of the angle formed by the lines connecting the edges of the aperture and the central axis of the head of the bone. Axes x and x' correspond to the lines connecting the edges of the aperture. Angle b is the angle formed by the lines connecting the edges of the aperture and the central axis of the head of the bone. Angle a is the angle formed by the interior bisector of angle b and one of the lines connecting the edges of the aperture. Angle c corresponds to the angle by which the bone neck is spanned by the cutting component.

In particular embodiments, the one or more of the parts of the collar of the guiding tools according to the invention at least partially span the contour of the bone neck. FIG. 3 shows a schematic drawing (A) of a bone head (1) and neck (2), according to a particular embodiment of the invention, as well as two cross-sectional views of the neck (2). The dotted lines schematically represent the outline of the guiding tool according to the invention when positioned on the bone head (3).

In specific embodiments, the one or more parts of the collar span the contour of the bone neck over about 180° (angle "c" of FIGS. 3B and C, where angle c would be about 180°). In further particular embodiments, the collar comprises one part which spans the contour of the neck of the bone over about 180° (see FIGS. 3B and C, where angle c is about 180°).

In alternative embodiments, the one or more parts of the collar span the contour of the neck over less than 180°. Indeed, the minimal requirement for the collar is that it supports at least one patient-specific part, which need not span the contour of the neck over 180°.

In further embodiments, the one or more parts of the collar span the contour of the bone neck over more than 180° (angle c is more than 180°), maintaining an opening for passage of the bone neck at least its smallest diameter. In these embodiments an overhang of the ends of the collar is created when the guiding tool is placed on the bone head (forming an "undercut") at the neck. By spanning the contour of the bone neck by more than 180°, the collar provides extra support and stability to the surgical tools of the invention as the bone neck is clasped into the guiding tool. In particular embodiments, the collar spans the contour of the bone neck over about 180° to 220° (see FIGS. 3B and C, where angle c would be about 180 to about 220°).

According to particular embodiments, the collar comprises more than one part, whereby one part can be released forming an opening which allows placement of the collar on the bone neck. After the placement of the guiding tool onto the bone, the collar can be closed by means of the releasable part such that the collar fully encloses the contour of the bone neck.

The size and shape of the one or more parts of the collar are not critical to the invention, provided that they support at least one patient-specific part. In particular embodiments, the one or more parts of the collar of the neck are rectangular in shape and typically have a height of between 2 and 20 mm (in the direction of the longitudinal axis of the neck) and each or together span between 5° and 220° of the contour of the neck (see FIGS. 3B and C, where angle c is between 5° and 220°), typically corresponding to a length of between 1 to 15 cm.

In particular embodiments, the one or more parts of the collar span the contour of the bone neck for about 180° to 220° (see FIGS. 3B and C, where angle c is about 180° to 220°) whereby the central axis of the neck of the bone when the tool is placed on the neck of the bone corresponds to the central axis of the collar. In particular embodiments, where the central axis of the bone head corresponds to the central axis of the neck, the central axis of the guiding tool corresponds to the central axis of the collar (oriented perpendicular to the cross-section the collar).

As indicated above, in order to allow placement of the surgical guiding tools of the invention on the bone neck, the collar comprises at least one opening which allows passage of the bone neck at least its smallest diameter. Accordingly, where the collar of the guiding tools according to the present invention spans the contour of the neck of the bone over more than 180° (see FIGS. 3B and C, where angle c is more than 180°), the collar retains an opening which allows passage of the neck at least its smallest diameter.

According to particular embodiments and as further described herein, the neck of the bone on which the tool is to be placed is ellipsoid, with a longitudinal (transverse or major) axis or diameter and a minor or conjugate diameter. In such cases, the cross-section of the collar (perpendicular to the axis of the guiding tool) which spans the neck will also be ellipsoid (or a part thereof), to closely fit the contour of the neck. In these embodiments, the size and the position of the opening in the collar will influence the placement of the guiding tool on the bone head. Indeed, where the opening spans over 160° or more, more particularly 180° or more of the contour of the bone neck (see FIGS. 3B and C, where angle b is about 160° or more and, more particularly, 180° or more) and thus the collar itself spans less than 180° of the bone neck (see FIGS. 3B and C, where angle c is less than 180°), or corresponds to the largest diameter of the neck, the guiding tool can be configured such that, if required, it can be placed directly on the bone head and neck, fitting immediately into its definite position. Indeed, it is envisaged that even where there is some overhang of the ends of the collar (i.e. opening limited to 160° of the contour of the neck), the flexibility of the material may make it possible to push the collar directly in its required position onto the bone neck.

FIG. 3 illustrates an embodiment of the guiding tools of the invention wherein the collar spans the contour of the bone neck (2) over an angle (c) of more than 180°. such as an angle (c) of 180° to 220° and the cross-section of the neck of the bone (and the corresponding collar) is ellipsoid. In this embodiment, the opening is configured such that it spans less than an angle (b) of 180° of the bone neck and the opening is positioned such that the (straight line connecting the ends of the) opening is parallel to the longitudinal or major axis of the ellipsoid cross-section of the collar (i.e. the longitudinal axis of the plane formed by the collar). The opening allows passage of the neck only through its minor axis, such that rotation of about 90° will be necessary during placement to align the major axis of the collar with the major axis of the bone neck thereby securing the collar onto the neck.

However, in particular embodiments of the guiding tools of the invention, the opening can be configured such that it spans less than 180°, more particularly less than 160° of the bone neck (see FIGS. 3B and C, where angle b is less than 180°, more particularly less than 160°) i.e. where the collar structure spans more than 180°, more particularly more than 200° (see FIGS. 3B and C, where angle c is more than 180°, more particularly more than 200°), more particularly such that it allows passage of the bone neck only by its minor axis. In those cases, and where the opening is positioned such that the (line connecting the ends of the) opening is not perpendicular to the major axis of the ellipsoid cross-section of the collar (i.e. the longitudinal axis of the plane formed by the collar), direct positioning of the collar on the neck is not possible, but placement will require rotation of the guiding tool on the bone head. After placement of the guiding tool on the bone head and neck, such an overhang of the collar provides extra support and stability to the surgical tools of the invention as the bone neck is clasped into the guiding tool.

In particular embodiments of the guiding tool according to the invention and as further described herein, the opening formed by the collar is positioned such that it (or the line connecting the ends of the opening) is parallel with the longitudinal or major axis of the plane formed by the collar. Where this opening allows passage of the neck only through its minor axis, rotation of about 90° will be necessary during placement to align the major axis of the collar with the major axis of the bone neck thereby securing the collar onto the neck. From this position, removal of the guiding tool from the bone head will again require a rotation combined with traction, so as to align the minor axis of the neck of the bone with the opening of the collar. Thus, in these embodiments, an additional securing function is ensured by the collar.

As described above, rotation of the guiding tool after placement on the bone head will result in the cutting elements cutting a groove into the cartilage on the surface of the bone head, in which the cutting elements are securely locked.

The surgical guiding tools of the present invention further comprise a guiding component for guiding a surgical instrument into the bone head of a patient. The guiding component contains at least one means of guiding an instrument such as but not limited to a drill, bur, saw, jig saw, lateral drill or any other cutting, milling or drilling instrument, the orientation and position of which corresponds to a pre-operative planning. The guiding component can optionally include safety stops to prevent a surgical instrument from advancing beyond a planned or determined depth into the bone.

Thus, where the surgical instrument is a drill or bur, the guiding component may comprise at least a cylindrical hole, the position and direction of which correspond to the pre-operatively planned drilling or burring trajectory. The diameter of the cylindrical hole will be at least the size of the diameter of the part of the surgical instrument, which is to be introduced in the bone.

In particular embodiments, where the surgical instrument is a saw, jig saw, mill or lateral drill, the guiding component may contain at least a (narrow) slot or flat surface, the position and orientation of which will correspond to the pre-operatively planned cutting plane or milling surface. The dimensions of the slot or surface will be such to allow passage or suitable guidance of the saw, jig saw, mill or lateral drill that is used.

Accordingly, in particular embodiments, the guiding component includes a cannula or channel through which at least part of a surgical instrument may be passed to engage the head of the bone at the desired location.

Typically, the guiding component is positioned on the connecting structure, which connects the guiding component of the tool with the cutting component and the collar. The guiding component is positioned on the connecting structure adjacent to the head of the bone such that a surgical instrument which is passed through the guiding component can engage the head of the bone at a desired location. The guiding component can be positioned in any direction with regard to the central axis of the head of the bone as long as it provides access to a surgical instrument for reaching the head of the bone at the desired location.

The central axis of the guiding component can be considered the axis of the guide, more particularly the axis of the planned trajectory of the surgical instrument. According to particular embodiments, the guiding component is positioned in the guiding tool such that the central axis of the guiding component is parallel to or forms an angle with the central axis of the bone head upon placement of the surgical guiding tool on the bone head.

Figure 4:
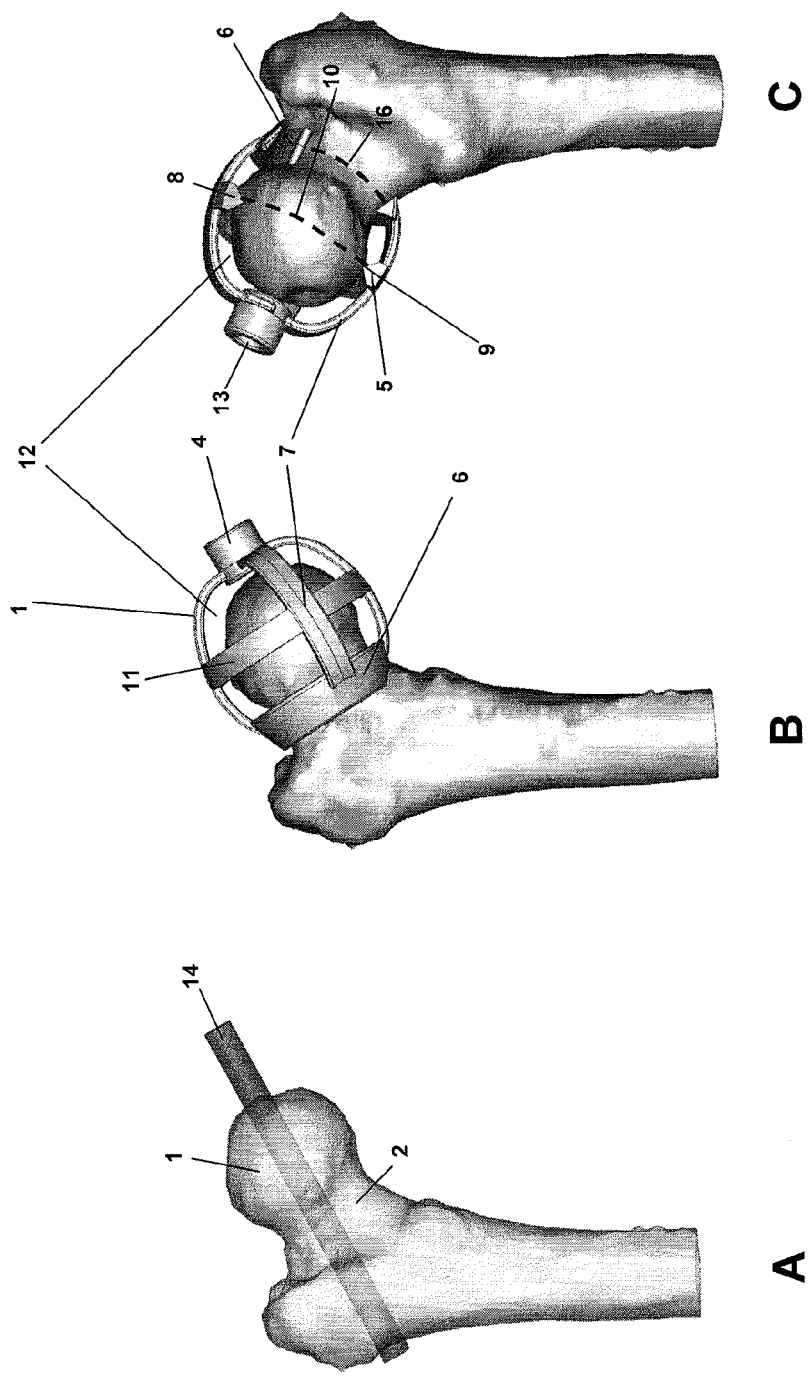
FIGS. 4A, 4B and C: Perspective views of femoral head and neck and placement of a guiding tool according to embodiments of the present invention thereon, wherein 1: femoral head, 2: femoral neck, 4: guiding component, 5: cutting element, 6: collar, 7: connecting element, 8: cutting element, 9: edge of a cutting element, 10: aperture, 11: connecting element, 12: cavity, 13: dill guide hole, 14: pre-operatively planned path or trajectory, 15: connecting element, 16: opening; A: Perspective view of a femoral head and neck indicating the pre-operatively planned path or trajectory (14) of a surgical instrument in the head of the femur, according to one embodiment of the invention. B and C: Different perspective views of a guiding tool according to a particular embodiment of the present invention when placed on a femur head and neck.

According to particular embodiments, the central axis of the guiding component is positioned in or in the extension of the central axis of the bone head upon placement of the surgical guiding tool on the bone head (see FIGS. 4, B and C).

According to particular embodiments, where the edges of the cutting elements of the cutting component of the guiding tool according to the present invention are all positioned in one or more parallel planes, the guiding component is positioned perpendicular to the one or more planes formed by the edges of the cutting element(s). The latter will ensure that the force applied when introducing the surgical instrument into the guiding component is perpendicular to the force of the cutting element(s) in the cartilage.

As mentioned above, the surgical guiding tools of the present invention further comprise a connecting structure, which directly or indirectly connects the collar to the cutting component and/or to the guiding component in the tools according to the invention. The connecting structure is hence such that the collar, the cutting component comprising the cutting element(s) and the guiding component are interconnected. The connecting structure typically comprises one or more connecting elements, which support the guiding component, cutting elements and/or the collar.

In particular embodiments, the connecting structure comprises two or more connecting elements or members which span the length of the guiding tool, running from the collar to the top of the bone head, forming the cavity around the bone head. longitudinally over the bone head, interconnecting at the top of the bone head (see, for example, FIG. 4, items 7 and 15). Such longitudinal connecting elements may each support one or more cutting elements. The cutting elements may also be supported by one or more connecting elements structures as rings spanning the contour of the bone head, whereby the transversal connecting elements or members are connected to the one or more rings (see, for example, FIG. 4, item 11).

As detailed above, the connecting structure forms at least one aperture starting from the opening in the collar, allowing the passage of the bone head and ensures placement of the guiding component on the bone head upon placement of the collar on the bone neck.

The connecting structure of the surgical guiding tools according to the present invention must be sufficiently rigid, so as not to ensure the desired stability and accuracy upon use of the guiding tool and should nevertheless be as open as possible, so as to allow the surgeon visual verification of the good fit of the surgical tool.

In particular embodiments the connection structure of the guiding tools according to the present invention ensure a rigid but flexible connection between the cutting component, guiding component and collar of the guiding tool, such that the position of the different components of the guiding tool relative to each other is fixed. However, in particular embodiments the guiding tool can be configured so as to allow rotation of the cutting elements with respect to the collar. The rotation of the cutting elements on the bone head after placement allows the cutting of a groove into the bone head for additional stability. This feature can be incorporated into the tool in different ways, known to the person skilled in the art. For instance, this can be ensured by connecting the collar and the connecting structure with a ridge (or protrusion) and groove structure. Such structures can define a very specific angle of rotation (in order to correspond to the pre-operative planning) and optionally include a mechanism for securing the parts in their definite positions (to ensure stability).

In particular embodiments, the present invention provides patient-specific surgical guiding tools for a femur head comprising (i) a guiding component for guiding a surgical instrument, (ii) a cutting component comprising one or more cutting element(s), positioned so as to cut in the cartilage of the femur head upon placement of the surgical guiding tool on the femur head, (iii) a collar spanning at least a part of the contour of the neck of the femur head but retaining an opening which allows passage of the neck at least its smallest diameter and comprising a patient-specific component, and (iv) a connecting structure connecting the collar to the cutting component and to the guiding component, such that the collar, the cutting component and the guiding component are interconnected. In the guiding tools according to these embodiments, the connecting structure forms at least one aperture allowing the passage of the femur head and ensuring placement of the guiding component on the femur head upon placement of the collar on the bone neck. Furthermore, in the guiding tools according to these embodiments, a cutting component comprising outer cutting elements are positioned each at a different side of the aperture and each at a maximal angle of 90° from the interior bisector of the angle formed by the lines connecting the edges of the aperture and the central axis of the femur head upon placement of the surgical guiding tool on the femur head.

In particular embodiments of the surgical guiding tool for a femur head, the edges of the one or more cutting elements are all positioned in the same plane, more particularly in a plane perpendicular to the position of the central axis of the femur head upon placement of the surgical guiding tool on the femur head.

In more particular embodiments, the central axis of the guiding component is positioned in or in the extension of the central axis of the femur head upon placement of the surgical guiding tool on the femur head, and the guiding component is positioned perpendicular to the plane formed by the edges of the outer cutting elements.

For the femur head, surgical guiding tools for either direct placement or for rotation placement are envisaged. In particular embodiments, where a tool for direct placement is envisaged, The outer cutting elements are positioned each at a different side of the aperture and each at an angle of about 80° from the interior bisector of the angle formed by the lines connecting the edges of the aperture and the central axis of the femur head. Accordingly, in these embodiments, the connecting structures, e.g. one or more ring structures, span the contour of the bone head by about 200° at the widest point of the femur head. Typically, the collar of the guiding tool spans the contour of the neck of the femur head over more than 180°. Before placement of such a device on the femur head, the guiding tool is oriented such that the patient-specific component in the collar is fitted directly on the patient-specific area of the neck upon placement.

In alternative embodiments, a tool for rotation placement is envisaged. Typically herein, the collar spans the neck of the femur head over more than 180° and the opening in the collar is positioned such that the axis connecting the ends of the opening is not perpendicular to the longitudinal axis of the ellipsoid plane formed by the collar. More particularly, the opening is positioned such that it is parallel with the longitudinal axis of the plane formed by the collar. In these embodiments of the guiding tools of the invention, the outer cutting elements are positioned each at a different side of the aperture and each at an angle of about 75° from the interior bisector of the angle formed by the lines connecting the edges of the aperture and the central axis of the femur head. Accordingly, in these embodiments, the connecting structures, e.g. one or more ring structures, span the contour of the bone head by about 210° at the widest point of the femur head. Before placement of such a device on the femur head, the guiding tool is oriented such that the patient-specific component in the collar is at an angle with its corresponding area on the neck and thus requires rotation of the device after placement to ensure interlocking.

A particular, non-limiting embodiment of the invention as described herein, is illustrated in FIG. 4. FIG. 4 shows in (A) the pre-operatively planned direction of the surgical tool in a femur head, according to a particular embodiment of the invention. FIGS. 4 B and C show perspective views of a surgical guiding tool designed so as to ensure appropriate guiding of a surgical instrument according to a particular embodiment of the present invention which is positioned on a femur head (1) and neck (2). More particularly, FIGS. 4 B and C illustrates a guiding tool (3) comprising a guiding component (4), a cutting component comprising cutting elements (e.g. 5 and 8), a collar (6) and a connecting structure comprising connecting elements (e.g. 7, 11, 15) defining the cavity (12) of the tool. The different components of the guiding tools according to this specific embodiment are described below in further detail. Reference to the position of the head and/or neck of the bone is intended to refer to the position of the head and/or neck of the bone, respectively, when the tool has been placed onto the bone head and neck.

The cutting component of the guiding tool according to the specific embodiment of FIGS. 4 B and C comprises two or more cutting elements (of which 5 and 8 are visible in FIGS. 4 B and C). The cutting elements are positioned along the contour of the inside of the surgical guiding tool such that they cut at different positions along the contour of the bone head (1) when the tool is placed thereon. Cutting elements 5 and 8 have a sharp edge which is directed to the central axis of the head of the bone ("z" in FIGS. 1 and 3), when the head is positioned inside the guiding tool. In this embodiment, the edges of cutting elements 5 and 8 lie in a plane, which makes a cross-section of the bone head at its largest width and which is perpendicular to the position of the central axis of the head of the bone when the head is positioned inside the guiding tool. The edges (e.g. 9) of cutting elements 5 and 8 are located at opposing sides of the aperture (10) of the tool. In the embodiment illustrated in FIGS. 4 B and C the cutting elements are interconnected by a connecting element which has a ring structure (11), which is part of the connecting structure of the guiding tool.

The collar (6) comprises an opening (16) which allows passage of the neck of the femur head (2). The collar is connected to a connecting element supporting the cutting elements (such as 5 and 8) and the guiding component (4) by connecting elements (7) which define the aperture (10) of the guiding tool.

The guiding component of the embodiment illustrated in FIGS. 4 B and C comprises a cylindrical hole (13), the position and direction of which correspond to the pre-operatively planned guiding trajectory (14, see FIG. 4A). In this embodiment, the guiding component (4) is positioned in the guiding tool such that the central axis of the guiding component is positioned in or in the extension of the central axis of the bone head (referred to as "z" in FIGS. 4B and 3B and C) upon placement of the surgical guiding tool on the bone head (1). Furthermore, in the embodiment illustrated in FIG. 4, the guiding component (and the trajectory (14) are positioned perpendicular to the plane formed by the edges of the two or more cutting elements.

A further aspect of the present invention provides methods for manufacturing a patient-specific surgical guiding tool for a surgical intervention on a bone head according to the invention. As indicated above, the guiding tools according to the invention are designed to closely fit around the bone head and neck of the bone requiring surgical intervention, such as to ensure stability of the guiding component, which is positioned within the guiding tool such as to guide a surgical instrument along a predetermined orientation. One of the advantages of the tools of the present invention is that they can be manufactured to ensure accurate positioning on the bone head without the need to segment the cartilage of the bone head.

The methods for producing the surgical guiding tools of the invention typically comprise the steps of:

(a) obtaining volume information of the neck and optionally of the bone head of the bone requiring surgical intervention;

(b) identifying and selecting one or more parts of the bone neck which contains sufficient features such that it is patient-specific;

(c) determining the appropriate position of the guiding component on the guiding tool; this is in particular embodiments based on the pre-operative planning the desired path of the surgical tool in the bone head; and (d) preparing a surgical guiding tool based on the information obtained in steps (a), (b) and (c).

In particular embodiments, the surgical guiding tools according to the invention are designed based on volume information of both the neck and the bone head. In alternative embodiments, the surgical guiding tools according to the invention comprise a collar comprising a patient-specific component (based on patient-specific information of the neck) and a connecting structure which is modular and can optionally be adjusted to ensure a tight fit onto the bone head.

More particularly, in methods of the present invention step (d) comprises preparing a surgical guiding tool wherein:
  (i) the position of the collar is determined based on the image of the bone neck obtained in step (a)
  (ii) the collar comprises a patient-specific component comprising at least one patient-specific area based on the patient-specific parts of the neck identified in step (b) and
  (iii) the guiding component is positioned in the surgical guiding tool such that, upon placement of the guiding tool on the bone head and neck, the guiding component is positioned as determined in step (c).

In further particular embodiments, step (d) comprises preparing a surgical guiding tool wherein the position of the connecting element, cutting component and collar is determined based on the image of the bone head and neck obtained in step (a).

Accordingly, step (a) of the methods of manufacturing the tools according to the invention comprises obtaining an image of the bone neck, and optionally of the bone head and neck. Digital patient-specific image information can be provided by any suitable means known in the art, such as for example a computer tomography (CT) scanner, a magnetic resonance imaging (MRI) scanner or an ultrasound scanner. A summary of medical imaging has been described in "Fundamentals of Medical imaging", by P. Suetens, Cambridge University Press, 2002. However, it is an advantage of the tools of the present invention that sufficient information can be obtained for designing the guiding tools of the invention based on either CT or MRI images without the need to segment the cartilage.

The methods for manufacturing the surgical guiding tools according to the invention further comprise the step of identifying and selecting at least one part of the bone neck which contains sufficient features such that it is patient-specific. Indeed, an important aspect of the guiding tools of the invention is the presence of one or more patient-specific areas in the collar of the tool, which interlock(s) with the corresponding region(s) in the neck upon placement of the tool on the bone head and ensure accurate positioning of the tool. As indicated above, the patient-specific regions of the neck may comprise specific anatomical features or may be modified to introduce specific features. The production of the one or more patient-specific areas for the collar requires detailed, geometrical patient-specific information in order to determine those surfaces of the bone neck that are suitable for this purpose.

Typically step (a) of the methods described above comprises the step of (a1) obtaining a 2D dataset of the head and neck of the bone and (a2) reconstructing a 3d virtual bone model (or part thereof) from said 2D datasets. Indeed, the first step in pre-operative planning is the construction of a 3D virtual model of the bone (or a part thereof). This reconstruction starts with sending a patient to a radiologist for scanning, e.g. for a scan that generates medical volumetric data, such as a CT, MRI scan or the like. The output of the scan can be a stack of two-dimensional (2D) slices forming a 3D data set. The output of the scan can be digitally imported into a computer program and may be converted using algorithms known in the field image processing technology to produce a 3D computer model of a relevant bone. Preferably, a virtual 3D model is constructed from the dataset using a computer program such as Mimics™ as supplied by Materialise N.V., Leuven, Belgium. A more detailed description for making a perfected model is disclosed in U.S. Pat. No. 5,768,134 entitled 'Method for making a perfected medical model on the basis of digital image information of a part of the body'.

Once the 3D volume of the bone (or a part thereof) is reconstructed, the surgeon (or person skilled in the art) can define the preferred position, orientation, depth and diameter of the bores and drill paths associated to them.

In particular embodiments, the methods of the invention further comprise the step of defining a central axis for the surgical guide. In a particular embodiment, the inertia axis of the bone head (and neck) is chosen for this. Defining the inertia axis of the femur may be done in a manual or (semi-)automatic way, using e.g. the position of anatomical landmarks. As an example, the inertia axis of a femur can be defined as follows: first, a sphere is fitted through the femur head using software such as e.g. Mimics. The centre of the sphere defines a first point of the inertia axis. The second point of the axis may be defined as the point in the lateral trochanteric area located 1, 1.5 or 2 cm below the point where the facet of the gluteus minimus muscle and the gluteus medius muscle intersect.

Having defined the preferred position, orientation, depth and diameter of the bores and drill paths associated to them, this information can then be transferred to a surgical guide template that fits perfectly when placed on the bone. A surgical template for use in general or specific surgical procedures may be defined as any object for placement on a unique and preferably stable position, specific for a patient and intended to be used for guiding a tool, an appliance or a medical or surgical device according to a prior determined position, direction and/or path and/or depth. A preferred method for designing the surgical template uses a computer program such as 3-matic™ as supplied by Materialise N.V., Leuven, Belgium. In another preferred method, the surgical template is automatically generated based on said drill hole information. Preferably, this method uses a number of design parameters as an input including, but not limited to, the dimensions of the surgical tools as used by the medical practitioner, the contact area of the surgical template with the bone where the surgical tool is to be placed, the thickness of the template, the fixation type (e.g. the position, orientation and diameter of fixation passages, the size of the undercut).

The methods for manufacturing the surgical guiding tools according to the invention further comprise the step of determining the appropriate position of the guiding component with regard to the bone head. In particular embodiments, this is done based on the pre-operative planning of the desired path of the surgical tool in the bone head;

The orientation of the guiding component has to be such that the surgical instrument is guided in the predetermined direction. Pre-operative planning of the intervention by the treating physician makes it possible to determine the required path of the surgical instrument, and accordingly, the required orientation of the guiding component. The pre-operative planning of the surgical intervention is done using suitable dedicated software, based on suitable medical images (of which CT, MRI, are examples), taking into account factors like bone quality and proximity to nerve bundles/blood vessels or other anatomically sensitive objects. To plan and simulate the intervention, preoperative images are imported into a computer workstation running 3D software. These images are manipulated as 3D volumes. The result is a computer simulation of the intervention, which outputs a planning containing the information necessary for adapting the orientation of the guiding component.

A further step of the methods for manufacturing a guiding tool according to the invention comprises preparing a surgical guiding tool according to the present invention.

As detailed hereinabove, such a surgical guiding tool comprises
  (i) a guiding component for guiding a surgical instrument,
  (ii) a cutting component comprising one or more cutting elements, positioned so as to cut in the cartilage of the head of the bone upon placement of the surgical guiding tool on the bone head,
  (iii) a collar spanning at least a part of the contour of the neck of the bone but retaining an opening which allows passage of the neck at least its smallest diameter and comprising a patient-specific component, and
  (iv) a connecting structure connecting said collar to said cutting component and/or to said guiding component, such that said collar, said cutting component and said guiding component are interconnected;
wherein the connecting structure forms at least one aperture allowing the passage of the bone head and ensuring placement of the guiding component on the bone head upon placement of the collar on the bone neck, and
wherein the one or more cutting elements are positioned such that a cutting element is present at both sides of said at least one aperture and at a maximal angle of 90° from the interior bisector of the angle formed by the lines connecting the edges of the aperture and the central axis of the head of the bone upon placement of the surgical guiding tool on the bone head; more particularly, where the cutting component comprises at least two cutting elements, the at least two of the two or more cutting elements are positioned each at a different side of said at least one aperture and each at a maximal angle of 90° from the interior bisector of the angle formed by the lines connecting the edges of the aperture and the central axis of the head of the bone upon placement of the surgical guiding tool on the bone head.

In particular embodiments, the step of preparing a surgical guiding tool comprises designing the surgical guiding tool wherein: (i) the position of the collar and optionally also the position of the connecting element and cutting component and collar are determined based on the image of the bone neck and head obtained in step (a); (ii) the collar comprises a patient-specific component comprising at least one patient-specific area based on the patient-specific parts of the neck identified in step (b) and (iii) the guiding component is positioned in the surgical guiding tool such that, upon placement of the guiding tool on the bone head and neck, the guiding component is positioned as determined in step (c).

In particular embodiments, the step of preparing the surgical guiding tool implies producing and assembling the different parts of the surgical guiding tool according to the invention, i.e. producing a guiding component (as described herein), a cutting component comprising two or more cutting elements (as described herein), a collar comprising a patient-specific component (as described herein) and a connecting structure, which interconnects the different parts of the guiding tool. In particular embodiments, where one or more of the components of the guiding tools of the present invention are made of one piece, the step of "assembling" may correspond to combining the relevant information for the combined manufacture of the pieces involved.

More particularly, the step of preparing the surgical guiding tool can involve positioning the connecting elements, cutting components and collar such that the guiding tool fits onto the bone head. The position of the connecting structures is not critical, as long as it does not interfere with the surgical procedure, and is determined by the required position of the cutting elements and the collar. The cutting elements are positioned such that the cut into the cartilage on the surface of the bone head upon placement of the tool on the bone head. The collar is positioned such that it allows interlocking of the patient-specific area(s) with the corresponding region(s) on the bone neck. In particular embodiments, the step of positioning the different elements can be performed as part of the design of the device.

In particular embodiments, the methods of the present invention comprise preparing a collar comprising a patient-specific component comprising at least one patient-specific area based on the patient-specific parts of the neck identified as described above. The one or more patient-specific area(s) is(are) made by generating a surface which is complementary to a patient-specific surface of the bone neck of the patient. For converting a digital image information of a part of the body into a basic model, template or mould, of which at least a part perfectly shows the positive or negative form of at least a portion of the part of the body, any suitable technique known in the art can be used, such as for example the rapid prototyping technique as described hereinbelow.

In particular embodiments the step of preparing the surgical guiding tool comprises the production of one or more elements by rapid prototyping. In further particular embodiments, the step of preparing the surgical guiding tool comprises the production of the surgical guiding tool as defined in the present invention, by rapid prototyping.

Rapid prototyping includes all techniques whereby an object is built layer by layer or point per point by adding or hardening material (also called free-form manufacturing). The best known techniques of this type are stereolithography and related techniques, whereby for example a basin with liquid synthetic material is selectively cured layer by layer by means of a computer-controlled electromagnetic beam; selective laser sintering, whereby powder particles are sintered by means of an electromagnetic beam or are welded together according to a specific pattern; fused deposition modelling, whereby a synthetic material is fused and is stacked according to a line pattern; laminated object manufacturing, whereby layers of adhesive-coated paper, plastic, or metal laminates are successively glued together and cut to shape with a knife or laser cutter; or electron beam melting, whereby metal powder is melted layer per layer with an electron beam in a high vacuum.

In a particular embodiment, Rapid Prototyping and Manufacturing (RP&M) techniques, are used for manufacturing the surgical guiding tool. Rapid Prototyping and Manufacturing (RP&M) can be defined as a group of techniques used to quickly fabricate a scale model of an object typically using three-dimensional (3-D) computer aided design (CAD) data of the object. Currently, a multitude of Rapid Prototyping techniques is available, including stereo lithography (SLA), Selective Laser Sintering (SLS), Fused Deposition Modeling (FDM), foil-based techniques, etc.

A common feature of these techniques is that objects are typically built layer by layer. Stereo lithography, presently the most common RP&M technique, utilizes a vat of liquid photopolymer "resin" to build an object a layer at a time. On each layer, an electromagnetic ray, e.g. one or several laser beams which are computer-controlled, traces a specific pattern on the surface of the liquid resin that is defined by the two-dimensional cross-sections of the object to be formed. Exposure to the electromagnetic ray cures, or, solidifies the pattern traced on the resin and adheres it to the layer below. After a coat had been polymerized, the platform descends by a single layer thickness and a subsequent layer pattern is traced, adhering to the previous layer. A complete 3-D object is formed by this process.

Selective laser sintering (SLS) uses a high power laser or another focused heat source to sinter or weld small particles of plastic, metal, or ceramic powders into a mass representing the 3-dimensional object to be formed.

Fused deposition modeling (FDM) and related techniques make use of a temporary transition from a solid material to a liquid state, usually due to heating. The material is driven through an extrusion nozzle in a controlled way and deposited in the required place as described among others in U.S. Pat. No. 5,141,680.

Foil-based techniques fix coats to one another by means of gluing or photo polymerization or other techniques and cut the object from these coats or polymerize the object. Such a technique is described in U.S. Pat. No. 5,192,539.

Typically RP&M techniques start from a digital representation of the 3-D object to be formed. Generally, the digital is sliced into a series of cross-sectional layers which can be overlaid to form the object as a whole. The RP&M apparatus uses this data for building the object on a layer-by-layer basis. The cross-sectional data representing the layer data of the 3-D object may be generated using a computer system and computer aided design and manufacturing (CAD/CAM) software.

A selective laser sintering (SLS) apparatus is particularly preferred for the manufacture of the guiding template from a computer model. It should be understood however, that various types of rapid manufacturing and tooling may be used for accurately fabricating these surgical templates including, but not limited to, stereolithography (SLA), Fused Deposition Modeling (FDM) or milling.

The surgical guiding tools of the invention (or parts thereof) may be manufactured in different materials. Typically, only materials that are biocompatible (e.g. USP class VI compatible) with the human body are taken into account. Preferably the surgical template is formed from a heat-tolerable material allowing it to tolerate high-temperature sterilization. In the case SLS is used as a RP&M technique, the surgical template may be fabricated from a polyamide such as PA 2200 as supplied by EOS, Munich, Germany or any other material known by those skilled in the art may also be used.

It will be clear to the skilled person that the designing of a tool or part thereof for direct or rotational placement and with or without overhang (and the extent of the overhang) may put certain requirements on the material to be used. Indeed, both the clasping function of the cutting elements (and the supporting connecting structure) and of the collar and the rotational movement of the device over the bone head require a particular resilience of the material. Indeed, the combination of the chosen material and design should allow the user to manually press the guide over the head of the femur.

Prior to creating a basic model, additional artificial elements with a useful function can be added based on the digital information and possibly based on additional external information. The useful function of the element can be an indication of a physical parameter, such as a position, a direction, a length or an angle which are important during surgery or the shape of a bone elevation. This way, an artificial model, template or mould can be manufactured that uniquely fits onto, around or into the relevant anatomy of the patient and contains precise openings to guide surgical instruments (see for example WO 95/28688 "Method for making a perfected medical model on the basis of digital image information of a part of the body", Materialise N.V.).

In a further aspect, the present invention provides methods for using the surgical guiding tools according to the invention to ensure the correct placement of the guiding tool onto the bone head. Such methods are applied upon using the guiding tools of the invention for guiding the introduction of a surgical instrument into or contacting a surgical instrument with the bone head.

Accordingly one aspect of the invention relates to methods for accurate positioning of a surgical instrument onto, and optionally introducing a surgical instrument into a head of a limb bone comprising the steps of:
(a) providing a surgical guiding tool according to the present invention;
(b) securing the surgical guiding tool on the bone head and neck; and
(c) introducing the surgical instrument through the guiding component.

According to the present invention the methods for introducing a surgical instrument into a head of a limb bone comprise the step of providing a surgical instrument comprising
  (i) a guiding component for guiding a surgical instrument,
  (ii) a cutting component comprising two or more cutting elements, positioned so as to cut in the cartilage of the head of the bone upon placement of the surgical guiding tool on the bone head,
  (iii) a collar spanning at least a part of the contour of the neck of the bone but retaining an opening which allows passage of the neck at least its smallest diameter and comprising a patient-specific component, and
  (iv) a connecting structure connecting the collar to the cutting component and/or to said guiding component, such that said collar, said cutting component and the guiding component are interconnected;
wherein the connecting structure forms at least one aperture allowing the passage of the bone head and ensuring placement of the guiding component on the bone head upon placement of the collar on the bone neck, and
wherein the one or more cutting elements are positioned such that a cutting element is present at both sides of said at least one aperture and at a maximal angle of 90° from the interior bisector of the angle formed by the lines connecting the edges of the aperture and the central axis of the head of the bone upon placement of the surgical guiding tool on the bone head; more particularly, where the cutting component comprises at least two cutting elements, at least two of the two or more cutting elements are positioned each at a different side of said at least one aperture and each at a maximal angle of 90° from the interior bisector of the angle formed by the lines connecting the edges of the aperture and the central axis of the head of the bone upon placement of the surgical guiding tool on the bone head.

Methods for producing the surgical guiding tool according to the invention are detailed hereinabove.

The methods for accurately positioning a surgical instrument onto a head of a limb bone and/or introducing a surgical instrument into a head of a limb bone of the present invention further comprise the step of securing the surgical guiding tool on the bone head and neck.

More particularly, the step of securing the surgical guiding tool on the bone head and neck implies that the guiding tool is placed onto the patient's limb bone head in such a manner so as to allow accurate and stable placement and optionally introduction of a surgical instrument onto/into the head of the limb bone. The present invention envisages different methods of securing the guiding tools of the invention on the corresponding bone head, referred to as "direct placement" and "rotation placement" methods herein. As will be detailed below, most guiding tools described herein can be secured onto the bone head for which it was designed either by direct placement or rotation placement. However, in some embodiments, the particular configuration of the guiding tool requires that it is secured onto its final position by rotation, thus requiring rotation placement. It is noted in this regard that the placement of the surgical guiding tool on the bone head according to the present invention is temporary and as such does not represent a substantial physical intervention and does not entail a substantial health risk for the patient.

Figure 5:
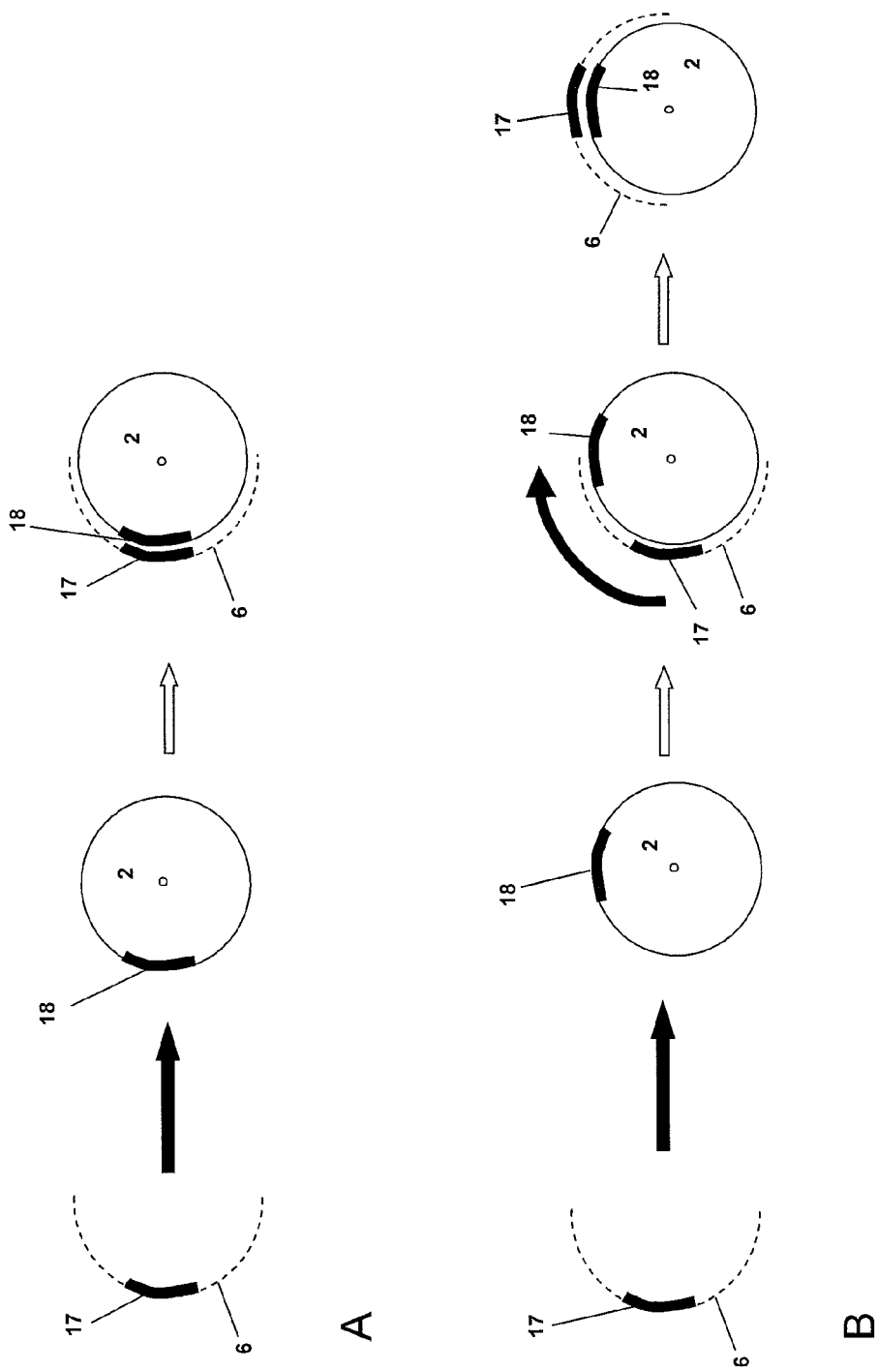
FIG. 5A: Schematic representation of the placement of the collar (6) of a guiding tool on a bone neck (2) according to particular embodiments of the invention. The full arrows indicate the movement of the tool. The tool is positioned prior to placement such that the patient-specific area (17) on the collar (6) is positioned parallel to its complementary patient-specific surface (18) present on the bone neck. When the collar is placed on the neck of the bone the patient-specific area (17) directly interlocks with its corresponding patient-specific surface on the bone neck.
FIG. 5B: Schematic drawing of the placement of the collar (6) of a guiding tool according to a particular embodiment of the invention on a bone neck (2); The full arrow indicates movement of the tool. The tool is positioned prior to placement such that the patient-specific area (17) on the collar (6) is at an angle with its complementary patient-specific surface (18) present on the neck of the bone. Then, the collar is placed over the neck of the bone. Finally, the collar is rotated over a particular angle, such as for example 90°, such that the patient-specific area of the collar (6) can interlock with its corresponding patient-specific surface on the bone neck.

In particular embodiments, the step of securing the surgical guiding tool on the bone head and neck is performed by direct placement. This implies that the guiding tool is placed onto the bone head by moving the bone head into the aperture and by ensuring that the patient-specific region of the neck corresponding to the patient-specific area of the collar are directly contacted upon placement. Typically, the guiding tool is moved towards the bone head such that the axes of the device and the bone head are parallel to each other, and the direction of movement is perpendicular to the central axis of the bone head. In these embodiments, no additional movements of the bone head in the guiding tool are necessary to ensure a tight fit of the tool on the bone head. Accordingly, in these embodiments of the methods of the invention, the placing step first comprises positioning the surgical guiding tool with the aperture (and opening) facing the bone head (and neck) such that the patient-specific component in the collar of the tool is positioned parallel to its complementary surface on the bone neck (FIG. 5A). Indeed, the patient-specific component of a guiding tool that is to be placed directly onto the bone without any additional (rotational) movement) has to be oriented in such a way that the one or more patient-specific areas will directly be contacted with the corresponding regions of the bone neck when the guiding tool is positioned onto the bone head. The step of positioning the tool on the bone head thus further comprises moving the surgical guiding tool over the bone head such that the central axis of the bone head is perpendicular to the direction of the movement until the patient-specific component of the collar locks into the complementary surface(s) of the neck of the bone, at the same time putting pressure on the cutting component so as to position it tightly on the bone head.

Indeed, upon placing the guiding tool over the bone head, the cutting elements or knife contacts are pushed into the cartilage of the bone head by applying pressure. Typically, the final position of the bone head is such that its central axis corresponds to the central axis of the device and/or the central axis of the cutting elements. Accordingly, in these embodiments, the surgical guiding tool is placed on the bone head by: (i) moving the bone neck through the opening of the bone-supported collar in a direction perpendicular to the central axis of the bone head and neck and (ii) introducing the cutting components comprising the cutting elements into the cartilage of the bone head by applying pressure. During this movement, the rigidity of the cutting component will provide the cutting elements or knife contacts at both sides of the aperture with opposing forces towards the surface of the cartilage of the bone head, thus supplying the pressure needed for the cutting elements to cut a groove in the cartilage of the bone head.

As detailed herein, the cutting elements and the supporting structures in the devices according to the invention maintain an aperture which allows passage of the bone head. Similarly, the collar, while it may span part of the contour of the neck in particular embodiments, maintains an opening for passage of the neck of the bone head. However, as further detailed herein, in particular embodiments the opening and the aperture may correspond to an angle of the bone head which is less than 180°. Where the material of the guiding tool is sufficiently resilient, this will nevertheless allow passage of the bone head and neck using some pressure. In those embodiments where the collar and/or cutting component span a segment of the bone neck and/or bone head larger than 180°, these structures will clasp around the bone head and neck, respectively such that the surgical tool is clasped into the cavity of the guiding tool and remains locked in position until deliberately removed by means of a strong pulling force on the surgical tool. Therefore, in particular embodiments of the methods of the invention, the surgical guiding tools are secured onto the bone with a higher stability, by making use of an overhang of the edges of the aperture of the surgical tools when placed on the bone head (accordingly forming an "undercut"). In these embodiments, the bone head is clasped into the guiding tool. In particular embodiments, the guiding tools designed for direct placement have an overhang which corresponds to 200°.

In particular embodiments, the placement of the surgical guiding tools of the present invention involves a rotational movement. According to these particular embodiment, the step of securing the tool onto the bone head first comprises positioning the surgical guiding tool with the aperture and the opening facing the bone head and neck such that the patient specific component of the collar is aligned at an angle with its complementary surface on the bone neck (FIG. 5B). This implies that when the surgical guiding tool is placed onto the bone head, the patient-specific area(s) of the collar is(are) not directly in contact with its corresponding surface of the neck of the bone. Again, typically, the guiding tool is moved towards the bone head such that the axes of the guiding tool and the bone head are parallel to each other, and the direction of movement is perpendicular to the central axis of the bone head and the movement until the bone head is positioned within the cavity of the device. Typically lateral movement stops when the central axis of the guiding tool aligns with the central axis of the bone head. However, in these embodiments, rotation of the guiding tool over the bone head is necessary to align the patient specific component with the corresponding structure(s) of the neck of the bone. Accordingly, in these embodiments, the placement of the guiding tool further comprises the step of rotating the surgical guiding tool to align the patient specific component of the collar with the corresponding region(s) of the neck of the bone such that these interlock. Typically, where the collar is tightly secured to the cutting elements, rotation of the collar implies rotation of the entire guiding tool and will require applying pressure on the cutting elements that are positioned at opposite sides of the aperture in the cartilage of the bone head. This results in the cutting of one or more grooves in the cartilage of the bone head by the cutting elements.

In further particular embodiments, more particularly where use is made of guiding tools which allow a rotational movement between the collar and the structure comprising the cutting elements, the placement of the tool comprises a rotational movement of only part of the tool after positioning on the bone head. Accordingly, in these embodiments, the placement step comprises positioning the surgical guiding tool with the aperture (and opening) facing the bone head (and neck) such that the patient-specific component in the collar of the tool is positioned parallel to its complementary surface on the bone neck and positioning the bone head into the aperture. In these embodiments, the patient-specific region(s) of the neck is(are) contacted directly with the corresponding patient-specific area(s) of the collar upon placement. However, in these embodiments of direct placement, part of the device comprising the cutting component is after placement.

As described above, in particular embodiments of the invention, the surgical guiding tools are tools which have been designed for use on a bone head of which the neck is ellipsoids in cross-section, such as the femur. More particularly, in specific embodiments of the guiding tools of the invention, the collar ellipsoid in cross-section and is designed to span the femur neck over more than 180°. In further particular embodiments of these tools, the opening of the collar is positioned such that the axis connecting the ends of the opening is not perpendicular to the longitudinal axis of the collar. More particularly the opening is positioned such that tit is parallel with the longitudinal axis of the (plane formed by) the collar. In these embodiments, the neck of the femur fits through the opening of the collar only in one direction, i.e. by passing the neck through by its minor axis. However, in order to fit the neck into its collar, rotation of the surgical tool is required.

Thus in particular embodiments, the methods of placing the surgical guiding tool of the invention on the bone head include the step of introducing the bone neck by its smallest diameter through the opening of the collar and placing the surgical guiding tool over the bone. The methods then further comprise rotating the surgical guiding tool to align the collar with the neck of the bone such that the patient-specific component of the collar locks into the complementary surface of the neck of the bone.

While rotating the guiding tool over the bone head, the cutting elements or knife contacts are introduced into the cartilage of the bone head by applying pressure. Accordingly, in these embodiments, the surgical guiding tool is placed on the bone by: (i) positioning the opening of the collar towards the bone neck at its smallest diameter and pushing the bone neck through the opening of the bone-supported collar and at the same time (ii) positioning the cutting components comprising the cutting elements on the cartilage of the bone head while applying pressure. According to these specific embodiments, the step of securing the tool onto the bone head further comprises rotating the surgical guiding tool to align the collar with the neck of the bone such that the patient-specific component of the collar locks into the complementary surface of the neck of the bone. Typically (but not necessarily), the surgical guiding tool is correctly positioned onto the bone head by turning the surgical tool into place by means of a rotation around a moving axis parallel to the central axis of the bone neck. Again, during this movement, the rigidity of the cutting component will provide the cutting elements or knife contacts at both sides of the aperture with opposing forces towards the surface of the cartilage of the bone head, thus supplying the pressure needed for the cutting elements to cut through the cartilage. The groove that is created by certain cutting elements during the rotational movement may accommodate other adjacently positioned cutting elements once the surgical guiding tool is put in place, providing additional stability.

Accordingly, the particular embodiments of the rotation placement methods described above are particularly suited when using surgical guiding tools that comprise a collar spanning the contour of the bone neck by more than 180° and which forms a plane having one longitudinal axis, wherein the opening (as described herein) is positioned such that the axis connecting the ends of the opening is not perpendicular to the longitudinal axis of the plane formed by the collar. More particularly, guiding tools wherein the axis connecting the ends of the opening is positioned such that it is parallel with the longitudinal axis of the plane formed by the collar are particularly suited for the methods of the present invention whereby placement of the guiding tool on the bone is performed by a rotational movement.

Again, the cutting elements and the supporting structures in the devices for use in the methods according to the invention maintain an aperture which allows passage of the bone head. Similarly, the collar, while it may span part of the contour of the neck in particular embodiments, maintains an opening for passage of the neck of the bone head. However, as further detailed hereinabove, in particular embodiments the opening and the aperture may correspond to an angle of the bone head which is less than 180°. Where the material of the guiding tool is sufficiently resilient, this will nevertheless allow passage of the bone head and neck using some pressure. In those embodiments where the collar and/or cutting component span a segment of the bone neck and/or bone head larger than 180°, these structures will clasp around the bone head and neck, respectively such that the surgical tool is clasped into the cavity of the guiding tool and remains locked in position until deliberately removed by means of a strong pulling force on the surgical tool. Therefore, in particular embodiments of the methods of the invention, the surgical guiding tools are secured onto the bone with a higher stability, by making use of an overhang of the edges of the aperture of the surgical tools when placed on the bone head (accordingly forming an "undercut"). In these embodiments, the bone head is clasped into the guiding tool. In particular embodiments, the guiding tools designed for rotational placement have an overhang which corresponds to 200°. However, it has been found that the stability of the devices which are designed for placement by rotational placement methods is further improved when the overhang f the cutting elements corresponds to 220°.

The methods for introducing a surgical instrument into a bone head according to the invention further comprise, after securing the surgical guiding tool on the bone head the step of introducing the surgical instrument through the guiding component. Thus, in the methods according to the present invention, the guiding component of the surgical guiding tools is positioned on a unique and stable position, specific for a patient and intended to be used for guiding a surgical instrument, according to a prior determined position, direction and/or path and/or depth. At least part of the surgical instrument is therefore introduced through a hole, a cannula, a channel or a slot or along a flat surface to engage the head of the bone at the desired location.

The surgical guiding tools and methods according to the present invention are applicable to limb bones, more particularly to major limb bones. Major limb bones as described herein are particularly long major limb bones, such as the femur, the tibia, the fibula, the humerus, the ulna, and the radius.

The guiding tools according to the present invention are designed for placement on the head and the neck or collar of a limb bone, more particularly of a major limb bone. Typically, the head of a limb bone is the expanded distal end or the upper rounded extremity of that bone, which fits into a cavity of another bone thereby making part of a joint. Typically, the neck (or collar) of a limb bone is a flattened pyramidal process of bone, connecting the bone head with the bone shaft and forming with the latter a wide angle opening medialward. The cross-section of the bone neck is generally ellipsoid, but can also be substantially circular. However, it will be understood by the skilled person that the guiding tools of the invention can also be applied on any extremity of a limb bone which comprises an expanded end piece and a more restricted area which is connected to the expanded end piece, even if this extremity is not generally referred to in the art as comprising a bone "head" and "neck".

The surgical guiding tools of the present invention are particularly suitable for use on the femur head. Accordingly, the surgical guiding tools of the invention are particularly suitable for introduction or contacting of surgical instruments into or with the femur (head) during hip surgery. The femur head (Latin: caput femoris) is the highest part of the thigh bone. It is supported by the femur neck. The head is globular and forms rather more than a hemisphere, is directed upward, medialward, and a little forward, the greater part of its convexity being above and in front. The femur neck (Latin: collum femoris) is a flattened pyramidal process of bone, connecting the femoral head with the femoral shaft.

The surgical guiding tools of the present invention are particularly suitable for guiding surgical tools with the object of drilling, cutting, sawing, milling, or performing a similar action on a bone head. Such interventions are typically required for performing bone-resurfacing, such as in hip resurfacing. Accordingly, the invention provides for tools according to the invention for use in bone resurfacing, more particularly bone resurfacing and methods of bone resurfacing which involve the guiding of a surgical instrument with the guiding tools according to the invention. It is clear to the skilled person that the tools of the present invention can be of use in any procedure which requires accurate positioning of a surgical tool in a bone head. In particular embodiments the invention provides methods of performing hip resurfacing on a patient in need thereof which methods comprise the step of placing a surgical guiding tool according to the invention on the femur head of the patient to ensure adequate guidance of a surgical instrument.

It will be appreciated by persons skilled in the art that numerous variations and/or modifications may be made to the invention without departing from the spirit or the scope of the invention as broadly described. The above described embodiments are, therefore, to be considered in all respects as illustrative and not restrictive.

The invention claimed is:

1. A patient-specific surgical guiding tool for a head and a neck of a major limb bone comprising:
   (i) a guiding component having a central axis for guiding a surgical instrument, wherein the surgical instrument has a central axis that corresponds to the central axis of the guiding component,
   (ii) a cutting component comprising two or more cutting elements having edges, the cutting component configured to be positioned so as to cut in the cartilage of the head of the bone upon placement of the surgical guiding tool on the bone head,
   (iii) a collar configured to span a contour of the neck of the major limb bone over about 180 degrees and further configured to retain an opening which allows passage of the neck at at least its smallest diameter and comprising a patient-specific component configured to directly interlock with a corresponding patient-specific surface on the neck of the major limb bone,
   (iv) a connecting structure configured to connect the collar to said cutting component and/or to said guiding component, such that said collar, said cutting component and said guiding component are interconnected; wherein said connecting structure forms at least one aperture configured to allow passage of the bone head and further configured to ensure placement of the guiding component on the bone head upon placement of the collar on the neck of the major limb bone, whereby lines connecting the edges of said aperture and said central axis of the guiding component form an angle for which an interior bisector can be determined,
   wherein the two or more cutting elements are positioned such that a cutting element is present at both sides of said at least one aperture and at a maximal angle of 90° from the interior bisector of the angle formed by the lines connecting the edges of the aperture and a central axis of the head of the bone upon placement of the surgical guiding tool on the major limb bone head,
   wherein the central axis of the guiding component is positioned in or in the extension of the central axis of the head of the major limb bone upon placement of the surgical guiding tool on the major limb bone head,
   wherein edges of said two or more cutting elements are positioned in a plane perpendicular to the central axis of the guiding component, and
   wherein said two or more cutting elements are interconnected by one or more ring structures configured to span the contour of the head of the major limb bone by at least 180 degrees.

2. The surgical guiding tool according to claim 1, wherein the edges of said two or more cutting elements are all positioned in the same plane.

3. The surgical tool of claim 1, wherein at least two of the two or more cutting elements are positioned each at a different side of the aperture and each at an angle of about 75° from the interior bisector of the angle formed by the lines connecting the edges of the aperture and the central axis of the head of the major limb bone.

4. The surgical tool of claim 1, wherein at least two of the two or more cutting elements are positioned each at a different side of the aperture and each at an angle of 80° from the interior bisector of the angle formed by the lines connecting the edges of the aperture and the central axis of the head of the major limb bone.

5. The surgical guiding tool according to claim 1, wherein said guiding component is positioned perpendicular to the plane formed by the edges of the two or more cutting elements.

6. The surgical guiding tool according to claim 1, wherein said collar spans the contour of the neck of the major limb bone over more than 180°.

7. The surgical guiding tool according to claim 1, wherein the collar spans the major limb bone neck over more than 180° and wherein the collar forms a plane with one longitudinal axis and said opening is positioned such that an axis connecting the ends of the opening is not perpendicular to the longitudinal axis of the plane formed by the collar.

8. The surgical guiding tool of claim 7, wherein the opening is positioned such that the axis connecting the ends of the opening is parallel with the longitudinal axis of the plane formed by the collar.

9. A method for manufacturing a patient-specific surgical guiding tool for a surgical intervention on a head of a major limb bone according to claim 1, said method comprising:
   (a) obtaining volume information from an image of the major limb bone neck and optionally the major limb bone head,
   (b) identifying and selecting one or more parts of the major limb bone neck, which contain sufficient features to be patient-specific,
   (c) determining an appropriate position of the guiding component with regard to the major limb bone head; and
   (d) preparing the surgical guiding tool wherein:
      (i) a position of the connecting structure, the cutting component and the collar is determined based on the image of the major limb bone head and neck obtained in step (a), (ii) the collar comprises a patient-specific component comprising at least one patient-specific area based on the patient-specific parts of the neck identified in step (b), and (iii) the guiding component is positioned in the surgical guiding tool such that, upon placement of the guiding tool on the major limb bone head and neck, the guiding component is positioned as determined in step (c).

10. A method for accurate positioning of a surgical instrument on a head of a major limb bone, which method comprises:

(a) providing a surgical guiding tool as defined in claim 1, whereby the patient-specific component is made complementary to a surface of the major limb bone neck of the patient, and the guiding component is designed to guide said surgical instrument in a predefined trajectory;

(b) securing the surgical guiding tool on the major limb bone head and neck by positioning the surgical guiding tool with the opening of the collar facing the major limb bone neck such that the patient specific component of the collar is aligned at an angle with its complementary surface on the major limb bone neck, moving the surgical guiding tool over the major limb bone head such that the central axis of the major limb bone head or neck is perpendicular to the direction of the movement until the tool is positioned over the major limb bone head and neck, rotating the surgical guiding tool to align the collar with the neck of the major limb bone such that the patient-specific component of the collar locks into the complementary surface of the neck of the major limb bone, thereby applying pressure on the two or more cutting elements that are positioned at opposite sides of the aperture so as to cut a groove in the cartilage of the major limb bone head; and (c) introducing the surgical instrument through the guiding component.

11. The method for accurate positioning of a surgical instrument onto a head of a major limb bone according to claim 10, which method comprises:

(a) providing a surgical guiding tool, whereby the patient-specific component is made complementary to a surface of the major limb bone neck of the patient, and the guiding component is designed to guide said surgical instrument in a predefined trajectory;

(b) securing the surgical guiding tool on the major limb bone head and neck by introducing the smallest diameter of the major limb bone neck through the opening of the collar and placing the surgical guiding tool over the major limb bone head; and rotating the surgical guiding tool to align the collar with the neck of the major limb bone such that the patient-specific component of the collar locks into the complementary surface of the neck of the major limb bone, thereby applying pressure on the two or more cutting elements that are positioned at opposite sides of the aperture so as to cut a groove in the cartilage of the major limb bone head; and (c) introducing the surgical instrument through the guiding component.

12. A method for the accurate positioning of an instrument onto a head of a major limb bone, which method comprises:

(a) providing a surgical guiding tool as defined in claim 1, whereby the patient-specific component is made complementary to a surface of the major limb bone neck of the patient and the guiding component is designed to guide said surgical instrument in a predefined trajectory;

(b) securing the surgical guiding tool on the major limb bone head and neck by positioning the surgical guiding tool with the opening of the collar facing the major limb bone neck such that the patient specific component of the collar is aligned in parallel with its complementary surface on the major limb bone neck, and moving the surgical guiding tool over the major limb bone head such that the central axis of the major limb bone head or neck is perpendicular to the direction of the movement until the patient-specific component of the collar locks into the complementary surface of the neck of the major limb bone, thereby applying pressure to said one or more cutting elements that are positioned at opposite sides of the aperture so as to cut a groove in the cartilage of the major limb bone head; and (c) introducing the surgical instrument through the guiding component.

* * * * *